United States Patent
Iyer et al.

(10) Patent No.: US 10,564,148 B2
(45) Date of Patent: Feb. 18, 2020

(54) MULTI-ORGAN MEDIA COMPOSITIONS AND METHODS OF THEIR USE

(71) Applicants: Los Alamos National Security, LLC, Los Alamos, NM (US); CFD RESEARCH CORPORATION, Huntsville, AL (US)

(72) Inventors: Rashi Iyer, Los Alamos, NM (US); Jennifer F. Harris, Los Alamos, NM (US); Jen-Huang Huang, Los Alamos, NM (US); Pulak Nath, Los Alamos, NM (US); Andrzej Przekwas, Huntsville, AL (US)

(73) Assignees: Triad National Security, LLC, Los Alamos, NM (US); CFD Research Corporation, Huntsville, AL (US)

( * ) Notice: Subject to any disclaimer, the term of this patent is extended or adjusted under 35 U.S.C. 154(b) by 0 days.

(21) Appl. No.: 15/513,948

(22) PCT Filed: Sep. 24, 2015

(86) PCT No.: PCT/US2015/052046
§ 371 (c)(1),
(2) Date: Mar. 23, 2017

(87) PCT Pub. No.: WO2016/049367
PCT Pub. Date: Mar. 31, 2016

(65) Prior Publication Data
US 2017/0275587 A1    Sep. 28, 2017

Related U.S. Application Data

(60) Provisional application No. 62/212,268, filed on Aug. 31, 2015, provisional application No. 62/106,510, filed on May 12, 2015, provisional application No. 62/054,843, filed on Sep. 24, 2014.

(51) Int. Cl.
*C12N 5/07* (2010.01)
*G01N 33/50* (2006.01)
*C12N 5/00* (2006.01)
*B01L 3/00* (2006.01)
*F16K 7/04* (2006.01)
*C12N 5/071* (2010.01)

(52) U.S. Cl.
CPC ........ *G01N 33/5064* (2013.01); *B01L 3/5027* (2013.01); *B01L 3/50273* (2013.01); *B01L 3/502707* (2013.01); *B01L 3/502715* (2013.01); *B01L 3/502738* (2013.01); *C12N 5/06* (2013.01); *G01N 33/5014* (2013.01); *G01N 33/5082* (2013.01); *B01L 2200/027* (2013.01); *B01L 2300/0627* (2013.01); *B01L 2300/0681* (2013.01); *B01L 2300/0832* (2013.01); *B01L 2300/0887* (2013.01); *B01L 2300/123* (2013.01); *B01L 2400/0481* (2013.01); *B01L 2400/0633* (2013.01); *C12N 5/067* (2013.01); *F16K 7/045* (2013.01); *G01N 33/5008* (2013.01)

(58) Field of Classification Search
CPC .... C12N 5/06; C12N 5/0602; G01N 33/5014; G01N 33/5008
USPC .......................................... 435/325, 404, 405
See application file for complete search history.

(56) References Cited

U.S. PATENT DOCUMENTS

| 4,108,725 | A  | * | 8/1978  | Kawaguchi ............ C07H 15/04 435/74 |
| 5,328,844 | A  | * | 7/1994  | Moore ................. C12N 5/0018 424/531 |
| 5,633,162 | A  |   | 5/1997  | Keen et al. |
| 5,650,317 | A  | * | 7/1997  | Chang .................. C12N 5/0631 435/371 |
| 6,197,575 | B1 |   | 3/2001  | Griffith et al. |
| 6,406,909 | B1 | * | 6/2002  | Shibuya ............... C12N 5/0043 435/383 |
| 6,900,056 | B2 |   | 5/2005  | Lee et al. |
| 7,863,035 | B2 |   | 1/2011  | Clemens et al. |
| 8,278,419 | B2 |   | 10/2012 | Jacobs |
| 8,580,546 | B2 |   | 11/2013 | Gonda et al. |
| 2004/0115801 | A1 | * | 6/2004 | Lin ...................... C12N 5/0679 435/325 |
| 2005/0051449 | A1 |   | 3/2005 | Jeter |

(Continued)

FOREIGN PATENT DOCUMENTS

| CN | 101220347 A * | 7/2008 | ............. C12N 5/073 |
| EP | 1516925 A1 * | 3/2005 | ........... C12N 5/0606 |

(Continued)

OTHER PUBLICATIONS

Zhao et al. Culture Medium Optimization for Photosynthetic Bacteria; Advanced Materials Research, vols. 113-116, pp. 1443-1446. (Year: 2010).*

(Continued)

*Primary Examiner* — Juliet C Switzer
*Assistant Examiner* — Paul C Martin
(74) *Attorney, Agent, or Firm* — Klarquist Sparkman, LLP

(57) ABSTRACT

Disclosed herein are media for culture of cells, tissues, and/or organs. The media formulations disclosed herein can be used to support growth, viability, and/or function of one or more than one cell type, tissue, or organ. In some embodiments, one or more cell types, tissues, organ devices, and/or organs are contacted with a disclosed culture medium under conditions sufficient to support growth, viability, and/or function of the cell types, tissues, and/or organs. The disclosed media can be used in methods of culturing multiple cell types, and in some examples, is used in a platform device including one or more organ devices, for example, by circulating the medium through the one or more organ devices in the platform.

20 Claims, 14 Drawing Sheets

(56) References Cited

U.S. PATENT DOCUMENTS

| | | |
|---|---|---|
| 2005/0130292 A1 | 6/2005 | Ahn et al. |
| 2007/0036809 A1* | 2/2007 | Michl .................. A61K 31/675 424/185.1 |
| 2007/0276508 A1 | 11/2007 | Fischer et al. |
| 2008/0019883 A1* | 1/2008 | Fike .................. C12N 1/00 422/139 |
| 2009/0016994 A1* | 1/2009 | Gibbs .................. C12N 5/0698 424/93.7 |
| 2010/0303687 A1 | 12/2010 | Blaga et al. |
| 2011/0215107 A1 | 9/2011 | Lee |
| 2012/0074062 A1 | 3/2012 | Jovanovic et al. |
| 2012/0135452 A1 | 5/2012 | Shuler et al. |
| 2012/0263631 A1 | 10/2012 | Masters et al. |
| 2013/0273643 A1 | 10/2013 | Vickers et al. |
| 2013/0309677 A1 | 11/2013 | Blackman et al. |
| 2014/0170693 A1 | 6/2014 | Ince |
| 2014/0356849 A1 | 12/2014 | Wikswo et al. |
| 2015/0004077 A1 | 1/2015 | Wikswo et al. |

FOREIGN PATENT DOCUMENTS

| | | |
|---|---|---|
| WO | WO 2013/085909 | 6/2013 |
| WO | WO 2013/086329 | 6/2013 |
| WO | WO 2013/086486 | 6/2013 |
| WO | WO 2013/086505 | 6/2013 |
| WO | WO 2013/181656 | 12/2013 |
| WO | WO 2014/081840 | 5/2014 |
| WO | WO 2014/127250 | 8/2014 |
| WO | WO 2015/006751 | 1/2015 |
| WO | WO 2015/138032 | 9/2015 |
| WO | WO 2015/138034 | 9/2015 |

OTHER PUBLICATIONS

International Search Report and Written Opinion issued for International Application No. PCT/US2015/052039 dated Dec. 22, 2015 (12 pages).

International Search Report and Written Opinion issued for International Application No. PCT/US2015/52043 dated Jan. 21, 2016 (12 pages).

International Search Report and Written Opinion issued for International Application No. PCT/US2015/052046 dated Nov. 12, 2015 (11 pages).

Tavana et al., "Microfluidics, Lung Surfactant, and Respiratory Disorders," *LabMedicine*, vol. 40, No. 4, pp. 204-209, 2009.

* cited by examiner

FIG. 3C
Medium 1
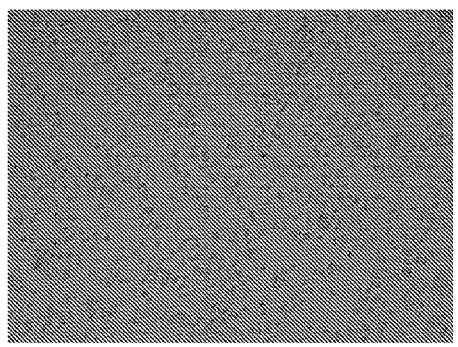
Medium 2
Control Medium
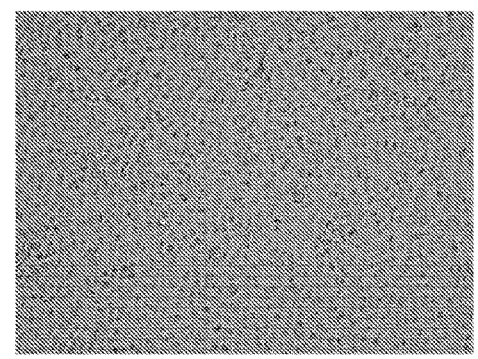
Medium 3
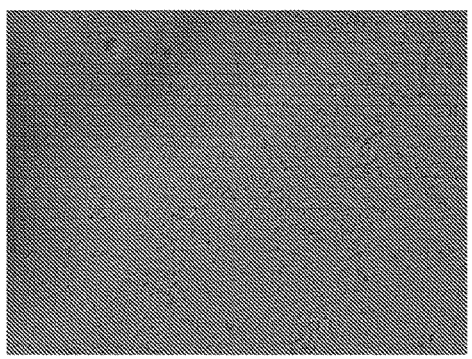
Medium 4
Medium 5
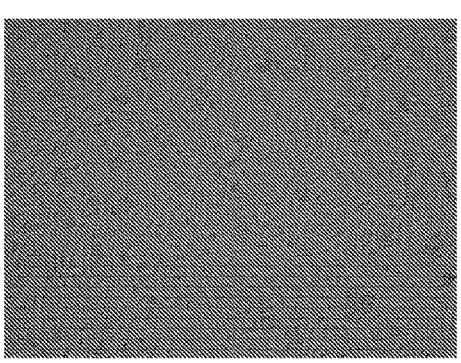

MULTI-ORGAN MEDIA COMPOSITIONS AND METHODS OF THEIR USE

CROSS REFERENCE TO RELATED APPLICATIONS

This is the § 371 U.S. National Stage of International Application No. PCT/US2015/052046, filed Sep. 24, 2015, which was published in English under PCT Article 21(2), which in turn claims the benefit of U.S. Provisional Application No. 62/054,843, filed Sep. 24, 2014; U.S. Provisional Application No. 62/160,510, filed May 12, 2015; and U.S. Provisional Application No. 62/212,268, filed Aug. 31, 2015, all of which are incorporated herein by reference in their entirety.

ACKNOWLEDGMENT OF GOVERNMENT SUPPORT

This invention was made with government support under Contract No. DE-AC52-06NA25396 awarded by the U.S. Department of Energy and grant number CMBXCEL-XLI-2-0001 awarded by the Defense Threat Reduction Agency (DTRA). The government has certain rights in the invention.

FIELD

This disclosure relates to the field of cell and tissue culture and in particular, to media formulations for culture of more than one cell or tissue type.

BACKGROUND

Organs consist of multiple cell types and multiple tissue types. For the last 70 years, increasingly specialized media have been developed for individual cells and tissue types. Media development has historically focused on developing formulations where the product is designed to grow cancerous cells as rapidly as possible. Much of the focus has been on supplying nutrients, regulating pH, and using frequent media changes to remove wastes.

Nature has devised a universal "medium," blood, which arguably can sustain a plethora of phenotypically and functionally distinct cell types. While blood can perform a plethora of functions in an animal or human, whole blood unfortunately becomes rapidly toxic in cell culture due to agglutination on account of cross-reactive white blood cells, and hemolysis from the short lifespan of red blood cells. So far, no available media formulation can perform all of the tasks that blood can perform.

SUMMARY

With the advent of multi-cellular culture systems, and the advances made in tissue models and developments in human-multi-organ-on-a-chip systems, there is a realization of the need for multi-cell type or multi-organ media (or even a "universal" media) that can be used to sustain multiple cell types simultaneously. There currently does not exist a universal serum-free media (or any universal medium for organs-on-a-chip or multi-organ platforms).

Disclosed herein are media that can be used for multiple cell and/or tissue types (such as two or more cell types or two or more tissues or organs). The disclosed media formulations are complex mixtures that can consist of up to 100 or more different components, including differing molarities of components such as inorganic salts and/or minerals, amino acids, energy-providing components, vitamins and/or cofactors, supplements, trace elements, organic acids, salts, and/or esters, antibiotics, and/or protein growth factors.

In one embodiment, the disclosed medium is an aqueous medium including NaCl, KCl, $CaCl_2 \cdot 2H_2O$, $NaH_2PO_4$, $MgSO_4$, $ZnSO_4 \cdot 7H_2O$, $Fe(NO_3)_3 \cdot 9H_2O$, L-arginine, L-leucine, L-isoleucine, glycine, L-phenylalanine, L-alanine, L-asparagine, L-serine, L-valine, L-histidine, L-proline, L-tryptophan, L-methionine, L-lysine, L-glutamic acid, L-cysteine, sodium pyruvate, niacinamide/nicotinamide, myoinositol/inositol, choline chloride, pyridoxine, thiamine, folic acid, D-calcium pantothenate, vitamin B-12, riboflavin, D-biotin, sodium bicarbonate, DL-6,8-thioctic acid/lipoic acid, transferrin, $CuSO_4 \cdot 5H_2O$, and $Na_2SeO_3$. The medium optionally includes glucose and/or phenol red. In some examples, glucose and/or phenol red are provided separately and added to the medium prior to use.

In another embodiment, the disclosed medium is an aqueous solution including NaCl, KCl, $CaCl_2 \cdot 2H_2O$, $NaH_2PO_4$, $MgSO_4$, $ZnSO_4 \cdot 7H_2O$, $Fe(NO_3)_3 \cdot 9H_2O$, $Na_2HPO_4$, $FeSO_4 \cdot 7H_2O$, $MgCl_2$, L-aspartic acid, L-arginine, L-leucine, L-isoleucine, glycine, L-phenylalanine, L-alanine, L-tyrosine disodium, L-asparagine, L-serine, L-valine, L-histidine, L-proline, L-alanyl-L-glu, L-tryptophan, L-methionine, L-lysine, L-glutamic acid, L-cysteine, L-glutamine, L-threonine, L-tyrosine disodium salt dihydrate, L-cystine, sodium pyruvate, D-fructose, D-galactose, D-sorbitol, sodium acetate anhydrous, niacinamide/nicotinamide, myoinositol/inositol, choline chloride, pyridoxine, thiamine, folic acid, D-calcium pantothenate, vitamin B-12, riboflavin, D-biotin, adenine, vitamin $D_2$, $Na_2EDTA \cdot H_2O$, D-pantothenic acid hemicalcium, putrescine, pyridoxal, D,L-tocopherol acetate, thymidine, vitamin A acetate, sodium propionate, linoleic acid, methyl linoleate, arachidonic acid, penicillin, sodium bicarbonate, DL-6,8-thioctic acid/lipoic acid, transferrin, xanthine, insulin, bovine serum albumin, VEGF, bFGF, triiodothyronine, HEPES free acid, TWEEN®-80 (polyoxyethylene 20 sorbitan monooleate), hypoxanthine, uracil, retinoic acid, EGF, hydrocortisone, ethanolamine, glucagon (such as human recombinant glucagon), bovine pituitary extract, epinephrine, phosphorylethanolamine, silicon, vanadium, manganese, molybdenum, $NiSO_4$, tin, $CuSO_4 \cdot 5H_2O$, $GeO_2$, $CrK(SO_4)_2$, $AlCl_3$, $MnCl_2$, KI, $NiCl_2$, KBr, $Na_2MoO_4$, $Na_2SeO_3$, RbCl, AgCl, and $CoCl_2$. The medium optionally includes glucose and/or phenol red.

In a further embodiment, the disclosed medium is an aqueous solution including NaCl, KCl, $CaCl_2 \cdot 2H_2O$, $NaH_2PO_4$, $MgSO_4$, $ZnSO_4 \cdot 7H_2O$, $Fe(NO_3)_3 \cdot 9H_2O$, $Na_2HPO_4$, $FeSO_4 \cdot 7H_2O$, $MgCl_2$, L-aspartic acid, L-arginine, L-leucine, L-isoleucine, glycine, L-phenylalanine, L-alanine, L-tyrosine disodium, L-asparagine, L-serine, L-valine, L-histidine, L-proline, L-alanyl-L-glu, L-tryptophan, L-methionine, L-lysine, L-glutamic acid, L-cysteine, L-glutamine, L-threonine, L-tyrosine disodium salt dihydrate, L-cystine, sodium pyruvate, D-fructose, D-galactose, D-sorbitol, sodium acetate anhydrous, niacinamide/nicotinamide, myoinositol/inositol, choline chloride, pyridoxine, thiamine, folic acid, D-calcium pantothenate, vitamin B-12, riboflavin, D-biotin, vitamin $D_2$, $Na_2EDTA \cdot H_2O$, putrescine, pyridoxal, D,L-tocopherol acetate, thymidine, vitamin A acetate, sodium propionate, linoleic acid, methyl linoleate, arachidonic acid, penicillin, sodium bicarbonate, DL-6,8-thioctic acid/lipoic acid, transferrin, xanthine, insulin, bovine serum albumin, VEGF, bFGF, triiodothyronine, glucagon (such as human recombinant glucagon), vanadium, manganese, tin, $CuSO_4 \cdot 5H_2O$, $GeO_2$, $CrK(SO_4)_2$, AlCl$_3$, MnCl$_2$, KI, NiCl$_2$, KBr, Na$_2$MoO$_4$, Na$_2$SeO$_3$, RbCl, AgCl, and CoCl$_2$. The medium optionally includes glucose and/or phenol red.

Also disclosed herein are methods of cell, tissue, or organ culture that include contacting one or more cell types, one or more tissues, and/or one or more organs with a disclosed medium (including, but not limited to the exemplary media of Table 1) under conditions sufficient to maintain viability, function, and/or growth of the one or more cell types, tissues, and/or organs.

In some embodiments, the methods include contacting one or more organ devices (such as one or more bio-assessment devices, for example, one or more of a lung organ device, a liver organ device, a heart organ device, and a kidney organ device) with a disclosed medium, for example, by circulating or perfusing a medium through the one or more organ devices. In some examples, two or more organ devices are included in a platform device, including two or more organ devices that are fluidly coupled. Thus, in some examples, the methods include perfusing an organ device with a disclosed medium where the organ device is fluidly coupled to a platform device including an organ perfusion system in fluid communication with the organ device, one or more pumps capable of pumping fluid (such as the medium) to one or more valves, a perfusion controller in electrical communication with the organ perfusion system, and optionally an analyzer, sensor, or combination thereof. In some examples, the perfusion system includes a fresh media circuit by which the medium is introduced. In other examples, the methods include delivering a disclosed medium to a reactor (such as an organ device) using a fluid management system including one or more channel substrates including one or more channels, a connection substrate including one or more inlets and/or outlets, a valving system including one or more valves positioned off-plane of the connection substrate and fluidly coupled to one or more channels, and a reservoir including one or more chambers for housing a fluid and one or more ports for delivering fluid to or from the one or more chambers, wherein the fluid management device is fluidly coupled with the reactor and the medium is housed in a chamber of the reservoir.

The foregoing and other features of the disclosure will become more apparent from the following detailed description, which proceeds with reference to the accompanying figures.

BRIEF DESCRIPTION OF THE DRAWINGS

FIGS. 3A-3C are a series of panels showing the effect of various media formulation on human primary mixed renal epithelial (NHRE) cells. FIG. 3A is a graph showing cytotoxicity after 7 days of culture in the indicated media. FIG. 3B is a graph showing cell viability after 7 days of culture in the indicated media. Control media is RenaLife™ medium (Lifeline Cell Technology, Frederick, Md.). "Triton-X" or "Triton control" indicates cells treated with Triton® X-100 surfactant to disrupt cell membranes and provide a positive control for cell leakage and/or death. FIG. 3C is a series of digital images of NHRE cells in the indicated media after 7 days of culture.

FIG. 7A is a graph showing lactate concentrations over 6 days of culture in the indicated media. FIG. 7B is a graph showing cell viability after 6 days of culture in the indicated media.

FIG. 7C is a series of digital images of cells in the indicated media after 6 days of culture. Control is Heparmed medium (Biochrom/Millipore, Berlin, Germany).

FIG. 8A shows lactate production (top), urea release (middle), and ammonia release (bottom) in cells cultured in control medium or Medium 5 throughout the 10 day period.

FIG. 8B shows lactate production (top), urea release (middle), and ammonia release (bottom) in cells cultured in control medium starting at day 1, with Medium 3 or Medium 5 added at a rate of 3 µl/minute on day 3 of culture.

DETAILED DESCRIPTION

Figure 1:
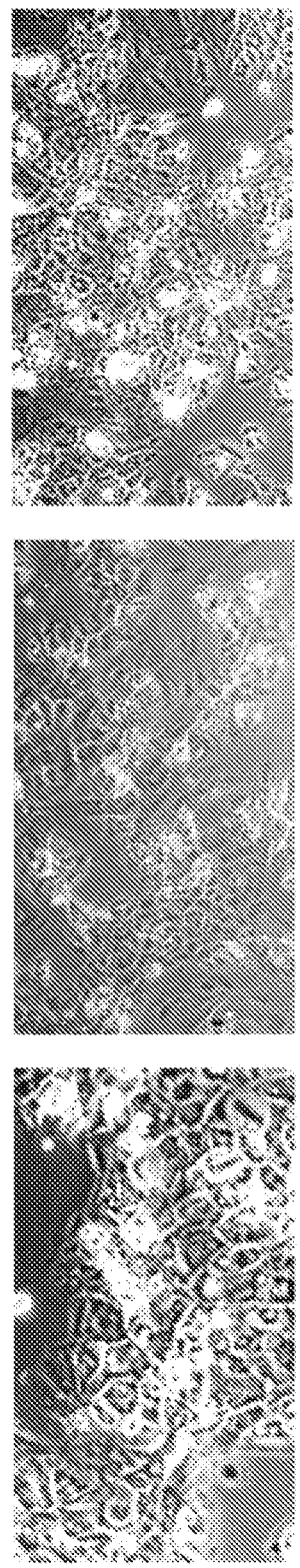
FIGS. 1A-1C are a series of digital images of Cor4U cardiomyocytes cultured in control Cor4U media (FIG. 1A), 50% Heparmed media (FIG. 1B), or 100% Heparmed media (FIG. 1C) after 14 days in culture. The cardiomyocytes beat in all media tested.

Standard cell culture media formulations perform many functions, including induction of cell proliferation, protein production, or virus production. As a result of this, cell culture media formulations are typically rich in components that may work well for one type of cells, but not another. Most cells in the human body are not designed to proliferate rapidly outside of injury, constantly secrete one single engineered protein, or be used as factories for high titer viral growth. Thus, the media that are commonly used on immortal cell lines may not be appropriate for primary cells.

Modern media formulations are extremely dense in glucose and amino acids to promote rapid growth. Additionally, media development has generally focused on the optimization of only 7-12 components. This is due to the large factorial space of testing multiple components in conjunction with each other. The disadvantages of current media formulations are several, including 1) media formulations are too "rich" for cells in a G0 state, 2) no media functions quite like human blood, 3) there is no oxygen-carrying capability, and 4) very few components are actually tested in media design.

Disclosed herein are formulations of cell culture media that can support function of one or more (such as 2, 3, 4, or more) cell, tissue, or organ types (including bio-assessment organ devices discussed herein). In some examples, the formulations are basal media, to which growth factors, sugars, and other components are added in a systematic manner to allow the growth and/or viability and function of several different human cell types. To achieve optimal cell functionality and longevity, additional components may be added to the basal media. In some examples, these include oxygen carriers, hormones, growth factors, protease inhibitors, protein hydrolysates, shear force protectors, proteins, vitamins, glutamine, trace elements, inorganic salts, minerals, lipids, and/or attachment factors.

I. Terms

Unless otherwise noted, technical terms are used according to conventional usage. Definitions of common terms in molecular biology may be found in *Lewin's Genes X*, ed. Krebs et al, Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics,* 3rd Edition, Springer, 2008 (ISBN: 1402067534).

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references cited herein are incorporated by reference. Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods.

In order to facilitate review of the various embodiments of the disclosure, the following explanations of specific terms are provided:

Cell Culture: Growth or maintenance of a population of cells in a defined set of conditions (such as culture medium, extracellular matrix, temperature, and/or time of culture) in vitro. In some examples, a cell culture includes a substantially pure culture. In additional examples a cell culture includes a mixed culture, such as co-culture of two or more types of cells. In further examples, a cell culture includes a tissue or organ construct.

Culture Medium: A synthetic set of culture conditions with the nutrients necessary to support the viability, function, and/or growth of a specific population of cells, a tissue, and/or an organ. Culture media generally include components such as a carbon source, a nitrogen source and a buffer to maintain pH. Additional components in culture media also may include one or more of oxygen carriers, hormones, growth factors, protease inhibitors, protein hydrolysates, shear force protectors, proteins, vitamins, glutamine, trace elements, inorganic salts, minerals, lipids, and/or attachment factors.

Organ or Tissue: A "tissue" includes a structure including cells (such as one or more cell types) that have similar structure and/or function. Examples of tissue types include epithelial, neuronal, muscle, endothelial or vascular, and/or connective tissue. An "organ" includes a structure including two or more tissue types that perform one or more particular functions. Exemplary organs include heart, lung, liver, kidney, brain, intestine, stomach, bone, skin, bladder, and pancreas. As utilized herein, "organ" also refers to an in vitro organ device (also referred to as a "bio-assessment" device) that includes two or more cell types and mimics or recapitulates one or more aspects of an organ, such as a lung, liver, heart, or kidney.

II. Media Formulations

Disclosed herein are media formulations that can support the growth, viability, and/or function of two or more cell types. In some embodiments, the media formulation(s) can support growth, viability, and/or function of the two or more cell types individually (for example, cell cultures of a single cell type), while in other embodiments, the media formulations can support growth, viability, and/or function of two or more cell types in a single culture (including but not limited to culture of a tissue, tissue model, or organ).

The disclosed media include components that support cell and/or tissue function, and in some instances reduce cytotoxicity to cells in culture. Components include combinations of inorganic salts and minerals (such as one or more of sodium salts, potassium salts, calcium salts, magnesium salts, zinc salts, iron salts, and/or buffers (for example, phosphate buffers)), amino acids (such as one or more L-amino acids, or dipeptides), energy sources or carbon sources (such as one or more of sodium pyruvate, fructose, galactose, sorbitol, glucose, and/or sodium acetate), vitamins and/or cofactors (such as nicotinamide/niacinamide, myoinositol/inositol, choline, pyridoxine, pyridoxal, thiamine, folic acid, pantothenate, pantothenic acid, vitamin B-12, riboflavin, biotin, adenine, vitamin $D_2$, EDTA, putrescine, tocopherol, thymidine, and/or vitamin A), organic acids, salts, and/or esters (such as propionate, linoleic acid, methyl linoleate, and/or arachidonic acid), antibiotics (for example, penicillin and/or streptomycin), supplements (such as bicarbonate, thioctic acid/lipoic acid, transferrin, xanthine, hypoxanthine, uracil, insulin, serum albumin, growth factors (such as VEGF, EGF, and/or FGF basic), buffers (such as HEPES), detergent (such as TWEEN® polysorbate detergent), triiodothyronine, retinoic acid, hydrocortisone, ethanolamine, phosphorylethanolamine, glucagon (such as human recombinant glucagon), pituitary extract, and/or epinephrine), and/or trace elements (such as silicon, vanadium, manganese, molybdenum, nickel, tin, copper, germanium, chromium, aluminum, potassium, selenium, rubidium, silver, and/or cobalt).

In one embodiment, a disclosed media (referred to herein as "Medium 1") is a "minimal" medium. Medium 1 is an aqueous solution including NaCl (e.g., 85-100 mM), KCl (e.g., 2-5 mM), $CaCl_2 \cdot 2H_2O$ (e.g., 0.5-2 mM), $NaH_2PO_4$ (e.g., 0.3-0.6 mM), $MgSO_4$ (e.g., 0.3-0.5 mM), $ZnSO_4 \cdot 7H_2O$ (e.g., 0.5-0.8 nM), $Fe(NO_3)_3 \cdot 9H_2O$ (e.g., 0.1-0.4 nM), L-arginine (e.g., 0.5-0.8 mM), L-leucine (e.g., 0.3-0.6 mM), L-isoleucine (e.g., 0.3-0.6 mM), glycine (e.g., 0.1-0.4 mM), L-phenylalanine (e.g., 0.1-0.4 mM), L-alanine (e.g., 0.04-0.06 mM), L-asparagine (e.g., 0.04-0.06 mM), L-serine (0.1-0.4 mM), L-valine (e.g., 0.1-0.4 mM), L-histidine (e.g., 0.05-0.3 mM), L-proline (e.g., 0.05-0.3 mM), L-tryptophan (e.g., 0.03-0.06 mM), L-methionine (e.g., 0.05-0.3 mM), L-lysine (e.g., 0.2-0.4 mM), L-glutamic acid (e.g., 0.04-0.06 mM), L-cysteine (e.g., 0.09-0.11 mM), sodium pyruvate (e.g., 0.1-0.4 mM), niacinamide/nicotinamide (e.g., 0.01-0.03 mM), myoinositollinositol (e.g., 0.01-0.03 mM), choline chloride (e.g., 0.01-0.03 mM), pyridoxine (e.g., 9-11 µM), thiamine (e.g., 4-7 µM), folic acid (e.g., 1-4 µM), D-calcium pantothenate (e.g., 1-4 µM), vitamin B-12 (e.g., 0.1-0.3 µM), riboflavin (e.g., 0.1-0.3 µM), D-biotin (e.g., 0.01-0.03 µM), sodium bicarbonate (e.g., 10-20 mµM), DL-6,8-thioctic acid/lipoic acid (e.g., 0.3-1 µM), transferrin (e.g., 0.1-0.4 mg/L), $CuSO_4 \cdot 5H_2O$ (e.g., 0.25-0.6 nµM), $Na_2SeO_3$ (e.g., 0.02-0.05 nµM).

In another embodiment, a disclosed media (referred to herein as "Medium 2") is an "expanded minimal" medium. Medium 2 is an aqueous solution including NaCl (e.g., 85-100 mM), KCl (e.g., 2-5 mM), $CaCl_2 \cdot 2H_2O$ (e.g., 0.5-2 mM), $NaH_2PO_4$ (e.g., 0.3-0.6 mM), $MgSO_4$ (e.g., 0.3-0.5 mM), $ZnSO_4 \cdot 7H_2O$ (e.g., 0.5-0.8 nM), $Fe(NO_3)_3 \cdot 9H_2O$ (e.g., 0.1-0.4 nM), $Na_2HPO_4$ (e.g., 0.3-0.6 mM), $FeSO_4 \cdot 7H_2O$ (e.g., 0.5-3 µM), $MgCl_2$ (e.g., 0.2-0.4 mM), L-aspartic acid (e.g., 0.01-0.03 mM), L-arginine (e.g., 0.5-0.8 mM), L-leucine (e.g., 0.3-0.6 mM), L-isoleucine (e.g., 0.3-0.6 mM), glycine (e.g., 0.1-0.4 mM), L-phenylalanine (e.g., 0.1-0.4 mM), L-alanine (e.g., 0.04-0.06 mM), L-tyrosine disodium (e.g., 0.01-0.03 mM), L-asparagine (e.g., 0.04-0.06 mM), L-serine (0.1-0.4 mM), L-valine (e.g., 0.1-0.4 mM), L-histidine (e.g., 0.05-0.3 mM), L-proline (e.g., 0.05-0.3 mM), L-alanyl-L-glu (e.g., 0.5-0.8 mM), L-tryptophan (e.g., 0.03-0.06 mM), L-methionine (e.g., 0.05-0.3 mM), L-lysine (e.g., 0.2-0.4 mM), L-glutamic acid (e.g., 0.04-0.06 mM), L-cysteine (e.g., 0.09-0.11 mM), L-glutamine (e.g., 1-3 mM), L-threonine (e.g., 0.3-0.6 mM), L-tyrosine disodium salt dihydrate (e.g., 0.1-0.4 mM), L-cystine (e.g., 0.05-0.2 mM), sodium pyruvate (e.g., 0.1-0.4 mM), D-fructose (e.g., 1-4 mM), D-galactose (e.g., 4-7 mM), D-sorbitol (e.g., 4-7 mM), sodium acetate anhydrous (e.g., 0.5-2 mM), niacinamide/nicotinamide (e.g., 0.01-0.03 mM), myoinositollinositol (e.g., 0.01-0.03 mM), choline chloride (e.g., 0.01-0.03 mM), pyridoxine (e.g., 9-11 µM), thiamine (e.g., 4-7 µM), folic acid (e.g., 1-4 µM), D-calcium pantothenate (e.g., 1-4 µM), vitamin B-12 (e.g., 0.1-0.3 µM), riboflavin (e.g., 0.1-0.3 µM), D-biotin (e.g., 0.01-0.03 µM), adenine (e.g., 0.08-0.1 mM), vitamin $D_2$ (e.g., 0.1-0.4 µM), $Na_2EDTA \cdot H_2O$ (e.g., 0.01-0.03 mM), D-pantothenic acid hemicalcium (e.g., 0.4-0.7 µM), putrescine (e.g., 0.4-0.7 µM), pyridoxal (e.g., 0.4-0.7 µM), D,L-tocopherol acetate (e.g., 0.01-0.03 µM), thymidine (e.g., 1-3 µM), vitamin A acetate (e.g., 0.1-0.5 µM), sodium propionate (e.g., 0.9-1.1 mM), linoleic acid (e.g., 0.1-1 µM), methyl linoleate (e.g., 0.01-0.1 µM), arachidonic acid (e.g., 0.01-0.1 mM), penicillin (e.g., 7-10 µM), sodium bicarbonate (e.g., 10-20 mM), DL-6,8-thioctic acid/lipoic acid (e.g., 0.3-1 µM), transferrin (e.g., 0.1-0.4 mg/L), xanthine (e.g., 1-3 µM), insulin (e.g., 0.7-1 nM), bovine serum albumin (e.g., 0.03-0.05 µM), VEGF (e.g., 0.005-0.03 µM), bFGF (e.g., 0.8-1.2 nM), triiodothyronine (e.g., 0.08-0.12 nM), HEPES free acid (e.g., 5-15 mM), TWEEN®-80 (polyoxyethylene 20 sorbitan monooleate) (e.g., 0.01-0.02 mM), hypoxanthine (e.g., 0.01-0.02 mM), uracil (e.g., 1-4 µM), retinoic acid (e.g., 0.08-0.11 µM), EGF (e.g., 0.4-0.6 nM), hydrocortisone (e.g., 0.02-0.05 µM), ethanolamine (e.g., 7-10 nM), glucagon (e.g., 0.7-1 nM), bovine pituitary extract (e.g., 0.005-0.02 mg/ml), epinephrine (e.g., 0.8-1.2 µM), phosphorylethanolamine (e.g., 0.4-0.6 µM), silicon (e.g., 0.04-0.06 mM), vanadium (e.g., 1-3 nM), manganese (e.g., 1-3 nM), molybdenum (e.g., 0.08-0.12 µM), $NiSO_4$ (e.g., 0.08-1.2 µM), tin (e.g., 2-4 nM), $CuSO_4 \cdot 5H_2O$ (e.g., 0.2-0.6 nM), $GeO_2$ (e.g., 1-4 nM), $CrK(SO_4)_2$ (e.g., 1-4 nM), $AlCl_3$ (e.g., 5-7 nM), $MnCl_2$ (e.g., 0.05-2 nM), KI (e.g., 0.3-0.6 nM), $NiCl_2$ (e.g., 0.3-0.6 nM), KBr (e.g., 0.1-0.3 nM), $Na_2MoO_4$ (e.g., 0.1-0.3 nM), $Na_2SeO_3$ (e.g., 0.02-0.05 nM), RbCl (e.g., 0.02-0.05 nM), AgCl (e.g., 0.01-0.03 nM), $CoCl_2$ (e.g., 7-10 pM).

In an additional embodiment, a disclosed medium (referred to herein as "Medium 3") is a "comprehensive" medium. Medium 3 is an aqueous solution including NaCl (e.g., 100-120 mM), KCl (e.g., 3-6 mM), $CaCl_2 \cdot 2H_2O$ (e.g., 0.5-2 mM), $NaH_2PO_4$ (e.g., 0.4-0.7 mM), $MgSO_4$ (e.g., 0.4-0.7 mM), $ZnSO_4 \cdot 7H_2O$ (e.g., 1-2 µM), $Fe(NO_3)_3 \cdot 9H_2O$ (e.g., 0.08-0.1 µM), $Na_2HPO_4$ (e.g., 0.3-0.6 mM), $FeSO_4 \cdot 7H_2O$ (e.g., 0.5-2 µM), $MgCl_2$ (e.g., 0.2-0.4 mM), L-aspartic acid (e.g., 0.6-0.9 mM), L-arginine (e.g., 0.8-2 mM), L-leucine (e.g., 0.8-2 mM), L-isoleucine (e.g., 0.8-2 mM), glycine (e.g., 0.5-0.8 mM), L-phenylalanine (e.g., 0.5-0.8 mM), L-alanine (e.g., 0.4-0.7 mM), L-tyrosine disodium (e.g., 0.3-0.6 mM), L-asparagine (e.g., 0.3-0.6 mM), L-serine (0.4-0.7 mM), L-valine (e.g., 0.4-0.7 mM), L-histidine (e.g., 0.1-0.5 mM), L-proline (e.g., 0.1-0.5 mM), L-alanyl-L-glu (e.g., 0.1-0.3 mM), L-tryptophan (e.g., 0.1-0.3 mM), L-methionine (e.g., 0.1-0.3 mM), L-lysine (e.g., 0.3-0.6 mM), L-glutamic acid (e.g., 0.08-0.2 mM), L-cysteine (e.g., 0.08-0.2 mM), L-glutamine (e.g., 1-3 mM), L-threonine (e.g., 0.2-0.5 mM), L-tyrosine disodium salt dihydrate (e.g., 0.1-0.4 mM), L-cystine (e.g., 0.05-0.09 mM), sodium pyruvate (e.g., 0.8-1 mM), D-fructose (e.g., 0.5-0.8 mM), D-galactose (e.g., 0.5-2 mM), D-sorbitol (e.g., 0.5-2 mM), sodium acetate anhydrous (e.g., 0.6-0.8 mM), niacinamide/nicotinamide (e.g., 0.02-0.05 mM), myoinositollinositol (e.g., 0.04-0.07 mM), choline chloride (e.g., 0.07-0.1 mM), pyridoxine (e.g., 9-11 µM), thiamine (e.g., 4-7 µM), folic acid (e.g., 3-6 µM), D-calcium pantothenate (e.g., 2-5 µM), vitamin B-12 (e.g., 0.2-0.5 µM), riboflavin (e.g., 0.3-0.6 µM), D-biotin (e.g., 0.4-0.7 µM), adenine (e.g., 0.01-0.04 mM), vitamin D2 (e.g., 0.05-0.08 µM), $Na_2EDTA \cdot H_2O$ (e.g., 3-6 µM), D-pantothenic acid hemicalcium (e.g., 0.1-0.3 µM), putrescine (e.g., 0.2-0.5 µM), pyridoxal (e.g., 0.1-0.3 µM), D,L-tocopherol acetate (e.g., 4-6 nM), thymidine (e.g., 1-3 µM), vitamin A acetate (e.g., 0.06-0.09 µM), sodium propionate (e.g., 0.1-0.4 mM), linoleic acid (e.g., 3-10 µM), methyl linoleate (e.g., 3-10 nM), arachidonic acid (e.g., 3-10 µM), penicillin (e.g., 0.07-0.1 mM), sodium bicarbonate (e.g., 15-25 mM), DL-6,8-thioctic acid/lipoic acid (e.g., 0.5-1.5 µM), transferrin (e.g., 2-5 mg/L), xanthine (e.g., 3-6 µM), insulin (e.g., 0.3-0.6 µM), bovine serum albumin (e.g., 1-3 µM), VEGF (e.g., 1-4 nM), bFGF (e.g., 0.1-0.4 nM), triiodothyronine (e.g., 1-4 nM), HEPES free acid (e.g., 2-10 mM), TWEEN®-80 (polyoxyethylene 20 sorbitan monooleate) (e.g., 2-5 µM), hypoxanthine (e.g., 2-5 µM), uracil (e.g., 0.5-0.8 µM), retinoic acid (e.g., 0.04-0.06 µM), EGF (e.g., 0.01-0.03 µM), hydrocortisone (e.g., 0.02-0.05 µM), ethanolamine (e.g., 0.1-0.3 µM), glucagon (e.g., 0.1-0.4 nM), bovine pituitary extract (e.g., 1-4 µg/ml), epinephrine (e.g., 0.1-0.4 µM), phosphorylethanolamine (e.g., 0.1-0.3 µM), silicon (e.g., 0.01-0.03 mM), vanadium (e.g., 0.1-0.3 µM), manganese (e.g., 0.01-0.04 µM), molybdenum (e.g., 0.01-0.04 µM), NiSO$_4$ (e.g., 0.01-0.04 µM), tin (e.g., 0.01-0.04 µM), CuSO$_4$.5H$_2$O (e.g., 2-6 nM), GeO$_2$ (e.g., 0.6-0.8 nM), CrK(SO$_4$)$_2$ (e.g., 0.5-0.7 nM), AlCl$_3$ (e.g., 1-3 nM), MnCl$_2$ (e.g., 0.1-0.4 nM), KI (e.g., 0.1-0.3 nM), NiCl$_2$ (e.g., 0.05-0.2 nM), KBr (e.g., 0.04-0.06 nM), Na$_2$MoO$_4$ (e.g., 0.04-0.06 nM), Na$_2$SeO$_3$ (e.g., 0.01-0.03 µM), RbCl (e.g., 7-9 µM), AgCl (e.g., 4-7 µM), CoCl$_2$ (e.g., 1-3 µM).

In another embodiment, a disclosed medium (referred to herein as "Medium 4") is a "heart and liver minimal" medium. Medium 4 is an aqueous solution including NaCl (e.g., 85-100 mM), KCl (e.g., 2-5 mM), CaCl$_2$.2H$_2$O (e.g., 0.5-2 mM), NaH$_2$PO$_4$ (e.g., 0.3-0.6 mM), MgSO$_4$ (e.g., 0.3-0.6 mM), ZnSO$_4$.7H$_2$O (e.g., 0.5-0.8 nM), Fe(NO$_3$)$_3$.9H$_2$O (e.g., 0.1-0.4 nM), Na$_2$HPO$_4$ (e.g., 0.3-0.6 mM), FeSO$_4$.7H$_2$O (e.g., 0.5-3 µM), MgCl$_2$ (e.g., 0.2-0.4 mM), L-aspartic acid (e.g., 0.03-0.06 mM), L-arginine (e.g., 0.5-0.8 mM), L-leucine (e.g., 0.3-0.6 mM), L-isoleucine (e.g., 0.3-0.6 mM), glycine (e.g., 0.1-0.4 mM), L-phenylalanine (e.g., 0.1-0.4 mM), L-alanine (e.g., 0.04-0.06 mM), L-tyrosine disodium (e.g., 0.5-3 mM), L-asparagine (e.g., 0.04-0.06 mM), L-serine (0.1-0.4 mM), L-valine (e.g., 0.1-0.4 mM), L-histidine (e.g., 0.1-0.4 mM), L-proline (e.g., 0.1-0.4 mM), L-alanyl-L-glu (e.g., 0.5-0.8 mM), L-tryptophan (e.g., 0.03-0.06 mM), L-methionine (e.g., 0.05-0.3 mM), L-lysine (e.g., 0.2-0.4 mM), L-glutamic acid (e.g., 0.04-0.06 mM), L-cysteine (e.g., 0.08-0.12 mM), L-glutamine (e.g., 1-4 mM), L-threonine (e.g., 0.3-0.6 mM), L-tyrosine disodium salt dihydrate (e.g., 0.1-0.4 mM), L-cystine (e.g., 0.05-0.2 mM), sodium pyruvate (e.g., 0.1-0.4 mM), D-fructose (e.g., 1-4 mM), D-galactose (e.g., 4-7 mM), D-sorbitol (e.g., 4-7 mM), sodium acetate anhydrous (e.g., 0.5-2 mM), niacinamide/nicotinamide (e.g., 0.01-0.03 mM), myoinositol/inositol (e.g., 0.01-0.03 mµM), choline chloride (e.g., 0.005-0.03 mµM), pyridoxine (e.g., 9-11 µM), thiamine (e.g., 4-7 µM), folic acid (e.g., 1-4 µM), D-calcium pantothenate (e.g., 1-4 µM), vitamin B-12 (e.g., 0.1-0.3 µM), riboflavin (e.g., 0.1-0.3 µM), D-biotin (e.g., 0.01-0.03 µM), vitamin D2 (e.g., 0.1-0.4 µM), Na$_2$EDTA.H$_2$O (e.g., 0.01-0.03 mM), putrescine (e.g., 0.4-0.7 µM), pyridoxal (e.g., 0.4-0.7 µM), D,L-tocopherol acetate (e.g., 0.01-0.03 µM), thymidine (e.g., 1-3 µM), vitamin A acetate (e.g., 0.1-0.5 µM), sodium propionate (e.g., 0.9-1.1 mM), linoleic acid (e.g., 0.1-1 µM), methyl linoleate (e.g., 0.01-0.1 µM), arachidonic acid (e.g., 0.01-0.1 mM), penicillin (e.g., 0.1-0.3 mM), sodium bicarbonate (e.g., 10-20 mM), DL-6,8-thioctic acid/lipoic acid (e.g., 0.3-1 µM), transferrin (e.g., 3-6 mg/L), xanthine (e.g., 0.01-0.03 mM), insulin (e.g., 0.5-2 µM), bovine serum albumin (e.g., 0.02-0.06 µM), VEGF (e.g., 0.005-0.03 µM), bFGF (e.g., 0.8-1.2 nM), triiodothyronine (e.g., 0.08-0.12 nM), glucagon (e.g., 0.7-0.9 nM), vanadium (e.g., 1-3 nM), manganese (e.g., 1-3 nM), tin (e.g., 2-4 nM), CuSO$_4$.5H$_2$O (e.g., 0.2-0.6 nM), GeO$_2$ (e.g., 1-4 nM), CrK(SO$_4$)$_2$ (e.g., 1-4 nM), AlCl$_3$ (e.g., 5-7 nM), MnCl$_2$ (e.g., 0.5-2 nM), KI (e.g., 0.3-0.6 nM), NiCl$_2$ (e.g., 0.3-0.6 nM), KBr (e.g., 0.1-0.3 nM), Na$_2$MoO$_4$ (e.g., 0.1-0.3 nM), Na$_2$SeO$_3$ (e.g., 0.02-0.05 nM), RbCl (e.g., 0.02-0.05 nM), AgCl (e.g., 0.01-0.03 nM), CoCl$_2$ (e.g., 7-10 µM).

In yet another embodiment, a disclosed medium (referred to herein as "Medium 5") is a "heart and liver comprehensive" medium. Medium 5 is an aqueous solution including NaCl (e.g., 95-125 mM), KCl (e.g., 2-6 mM), CaCl$_2$.2H$_2$O (e.g., 0.5-3 mM), NaH$_2$PO$_4$ (e.g., 0.5-0.9 mM), MgSO$_4$ (e.g., 0.4-0.8 mM), ZnSO$_4$.7H$_2$O (e.g., 0.5-0.9 µM), Fe(NO$_3$)$_3$.9H$_2$O (e.g., 0.04-0.08 µM), Na$_2$HPO$_4$ (e.g., 0.1-0.4 mM), FeSO$_4$.7H$_2$O (e.g., 0.6-0.9 µM), MgCl$_2$ (e.g., 0.05-0.3 mM), L-aspartic acid (e.g., 0.5-3 mM), L-arginine (e.g., 0.5-3 mM), L-leucine (e.g., 0.5-2.5 mM), L-isoleucine (e.g., 0.5-2.5 mM), glycine (e.g., 0.5-2.5 mM), L-phenylalanine (e.g., 0.5-2.5 mM), L-alanine (e.g., 0.5-2.5 mM), L-tyrosine disodium (e.g., 0.7-0.9 mM), L-asparagine (e.g., 0.6-0.9 mM), L-serine (0.5-0.8 mM), L-valine (e.g., 0.5-0.8 mM), L-histidine (e.g., 0.4-0.7 mM), L-proline (e.g., 0.4-0.7 mM), L-alanyl-L-glu (e.g., 0.1-0.5 mM), L-tryptophan (e.g., 0.1-0.4 mM), L-methionine (e.g., 0.1-0.4 mM), L-lysine (e.g., 0.2-0.6 mM), L-glutamic acid (e.g., 0.1-0.3 mM), L-cysteine (e.g., 0.05-0.2 mM), L-glutamine (e.g., 0.5-2.5 mM), L-threonine (e.g., 0.1-0.4 mM), L-tyrosine disodium salt dihydrate (e.g., 0.05-0.2 mM), L-cystine (e.g., 0.03-0.07 mM), sodium pyruvate (e.g., 0.5-3 mM), D-fructose (e.g., 0.5-3 mM), D-galactose (e.g., 1-4 mM), D-sorbitol (e.g., 1-4 mM), sodium acetate anhydrous (e.g., 0.3-0.7 mM), niacinamide/nicotinamide (e.g., 0.02-0.06 mM), myoinositollinositol (e.g., 0.02-0.06 mM), choline chloride (e.g., 0.01-0.05 mM), pyridoxine (e.g., 9-11 µM), thiamine (e.g., 4-7 µM), folic acid (e.g., 2-6 µM), D-calcium pantothenate (e.g., 2-5 µM), vitamin B-12 (e.g., 0.2-0.5 µM), riboflavin (e.g., 0.2-0.5 µM), D-biotin (e.g., 0.05-2 µM), vitamin D2 (e.g., 0.1-0.3 µM), Na$_2$EDTA.H$_2$O (e.g., 5-10 µM), putrescine (e.g., 0.1-0.4 µM), pyridoxal (e.g., 0.1-0.4 µM), D,L-tocopherol acetate (e.g., 0.01-0.03 µM), thymidine (e.g., 0.5-0.9 µM), vitamin A acetate (e.g., 0.1-0.4 µM), sodium propionate (e.g., 0.3-0.6 mM), linoleic acid (e.g., 6-20 µM), methyl linoleate (e.g., 6-20 nM), arachidonic acid (e.g., 6-20 µM), penicillin (e.g., 0.07-0.1 mM), sodium bicarbonate (e.g., 15-25 mM), DL-6,8-thioctic acid/lipoic acid (e.g., 0.5-1.5 µM), transferrin (e.g., 3-7 mg/L), xanthine (e.g., 5-9 µM), insulin (e.g., 0.3-0.7 µM), bovine serum albumin (e.g., 0.01-0.03 µM), VEGF (e.g., 3-7 nM), bFGF (e.g., 0.3-0.7 nM), triiodothyronine (e.g., 0.03-0.07 nM), glucagon (e.g., 0.2-0.6 nM), vanadium (e.g., 0.6-1 nM), manganese (e.g., 0.4-0.7 nM), tin (e.g., 0.5-2 nM), CuSO$_4$.5H$_2$O (e.g., 1-4 nM), GeO$_2$ (e.g., 0.5-2 nM), CrK(SO$_4$)$_2$ (e.g., 0.5-2 nM), AlCl$_3$ (e.g., 1-5 nM), MnCl$_2$ (e.g., 0.4-0.7 nM), KI (e.g., 0.1-0.4 nM), NiCl$_2$ (e.g., 0.1-0.4 nM), KBr (e.g., 0.05-0.2 nM), Na$_2$MoO$_4$ (e.g., 0.05-0.2 nM), Na$_2$SeO$_3$ (e.g., 0.01-0.03 µM), RbCl (e.g., 0.01-0.03 nM), AgCl (e.g., 0.005-0.03 nM), CoCl$_2$ (e.g., 2-6 µM).

In some non-limiting embodiments, the media disclosed herein are aqueous solutions comprising or consisting of the components listed in Table 1. In particular examples, the media comprise or consist of the formulations (components and amounts) shown in Table 1.

TABLE 1

Exemplary media formulations

| Category | Component | Concentration (mM)* | | | | |
|---|---|---|---|---|---|---|
| | | Medium 1 | Medium 2 | Medium 3 | Medium 4 | Medium 5 |
| Inorganic Salts & Minerals | NaCl | 9.20E+01 | 9.20E+01 | 1.10E+02 | 9.20E+01 | 1.06E+02 |
| | KCl | 3.43E+00 | 3.43E+00 | 4.29E+00 | 4.16E+00 | 4.76E+00 |
| | $CaCl_2 \cdot 2H_2O$ | 1.00E+00 | 1.00E+00 | 1.33E+00 | 1.05E+00 | 1.63E+00 |
| | $NaH_2PO_4$ | 4.53E-01 | 4.53E-01 | 5.92E-01 | 4.53E-01 | 7.31E-01 |
| | $MgSO_4$ | 4.07E-01 | 4.07E-01 | 5.08E-01 | 4.07E-01 | 6.09E-01 |
| | $ZnSO_4 \cdot 7H_2O$ | 6.96E-07 | 6.96E-07 | 1.50E-03 | 6.96E-07 | 7.50E-04 |
| | $Fe(NO_3)_3 \cdot 9H_2O$ | 2.48E-07 | 2.48E-07 | 9.29E-05 | 2.48E-07 | 6.20E-05 |
| | $Na_2HPO_4$ | | 5.00E-01 | 5.00E-01 | 5.00E-01 | 2.50E-01 |
| | $FeSO_4 \cdot 7H_2O$ | | 1.50E-03 | 1.12E-03 | 1.50E-03 | 7.50E-04 |
| | $MgCl_2$ | | 3.01E-01 | 3.01E-01 | 3.01E-01 | 1.51E-01 |
| Amino Acids | L-Aspartic acid | | 1.50E-02 | 7.66E-02 | 5.00E-02 | 1.53E+00 |
| | L-Arginine | 6.99E-01 | 6.99E-01 | 1.37E+00 | 6.99E-01 | 1.78E+00 |
| | L-Leucine | 4.50E-01 | 4.50E-01 | 1.08E+00 | 4.51E-01 | 1.48E+00 |
| | L-Isoleucine | 4.15E-01 | 4.15E-01 | 9.37E-01 | 4.16E-01 | 1.46E+00 |
| | Glycine | 2.50E-01 | 2.50E-01 | 6.88E-01 | 2.50E-01 | 1.13E+00 |
| | L-Phenylalanine | 2.15E-01 | 2.15E-01 | 6.65E-01 | 2.15E-01 | 1.11E+00 |
| | L-Alanine | 4.99E-02 | 4.99E-02 | 5.38E-01 | 5.00E-02 | 1.02E+00 |
| | L-Tyrosine disodium | | 1.68E-02 | 4.07E-01 | 1.61E+00 | 8.05E-01 |
| | L-Asparagine | 5.00E-02 | 5.00E-02 | 4.12E-01 | 5.00E-02 | 7.75E-01 |
| | L-Serine | 2.50E-01 | 2.50E-01 | 5.75E-01 | 2.50E-01 | 6.25E-01 |
| | L-Valine | 2.21E-01 | 2.21E-01 | 5.93E-01 | 2.21E-01 | 6.10E-01 |
| | L-Histidine | 1.50E-01 | 1.50E-01 | 3.70E-01 | 1.50E-01 | 5.75E-01 |
| | L-Proline | 1.50E-01 | 1.50E-01 | 3.63E-01 | 1.50E-01 | 5.75E-01 |
| | L-Alanyl-L-Glu | | 6.84E-01 | 1.71E-01 | 6.84E-01 | 3.42E-01 |
| | L-Tryptophan | 4.42E-02 | 4.42E-02 | 1.60E-01 | 4.42E-02 | 2.72E-01 |
| | L-Methionine | 1.16E-01 | 1.16E-01 | 1.66E-01 | 1.16E-01 | 2.09E-01 |
| | L-Lysine | 3.01E-01 | 3.01E-01 | 4.50E-01 | 3.01E-01 | 4.00E-01 |
| | L-Glutamic acid | 5.00E-02 | 5.00E-02 | 1.12E-01 | 5.00E-02 | 1.75E-01 |
| | L-Cysteine | 9.98E-02 | 9.98E-02 | 1.14E-01 | 9.98E-02 | 1.18E-01 |
| | L-Glutamine | | 2.00E+00 | 1.64E+00 | 2.56E+00 | 1.28E+00 |
| | L-Threonine | | 4.49E-01 | 3.49E-01 | 4.49E-01 | 2.25E-01 |
| | L-Tyrosine disodium salt dihydrate | | 1.99E-01 | 1.57E-01 | 2.14E-01 | 1.07E-01 |
| | L-Cystine | | 1.00E-01 | 7.51E-02 | 1.00E-01 | 5.00E-02 |
| Energy | Sodium pyruvate | 2.27E-01 | 2.27E-01 | 9.44E-01 | 2.27E-01 | 1.51E+00 |
| | D-Fructose | | 2.78E+00 | 6.95E-01 | 2.78E+00 | 1.39E+00 |
| | D-Galactose | | 5.55E+00 | 1.39E+00 | 5.55E+00 | 2.78E+00 |
| | D-Sorbitol | | 5.49E+00 | 1.37E+00 | 5.49E+00 | 2.75E+00 |
| | Sodium acetate anhydrous | | 1.00E+00 | 7.09E-01 | 1.00E+00 | 5.00E-01 |
| Vitamins & Co-factors | Niacinamide/Nicotinamide | 1.65E-02 | 1.65E-02 | 3.32E-02 | 1.66E-02 | 4.92E-02 |
| | Myoinositol/Inositol | 1.11E-02 | 1.11E-02 | 5.52E-02 | 1.11E-02 | 4.06E-02 |
| | Choline chloride | 1.07E-02 | 1.07E-02 | 8.55E-02 | 1.07E-02 | 3.74E-02 |
| | Pyridoxine | 9.71E-03 | 9.71E-03 | 9.83E-03 | 9.71E-03 | 9.79E-03 |
| | Thiamine | 6.43E-03 | 6.43E-03 | 6.43E-03 | 6.43E-03 | 6.43E-03 |
| | Folic acid | 2.27E-03 | 2.27E-03 | 4.93E-03 | 2.27E-03 | 4.14E-03 |
| | D-Calcium pantothenate | 2.10E-03 | 2.10E-03 | 3.92E-03 | 2.10E-03 | 3.40E-03 |
| | Vitamin B-12 | 1.48E-04 | 1.48E-04 | 3.26E-04 | 1.48E-04 | 3.25E-04 |
| | Riboflavin | 1.33E-04 | 1.33E-04 | 4.70E-04 | 1.33E-04 | 3.58E-04 |
| | D-Biotin | 1.43E-05 | 1.43E-05 | 5.30E-04 | 1.43E-05 | 1.03E-03 |
| | Adenine | | 9.00E-02 | 2.25E-02 | | |
| | Vitamin $D_2$ | | 2.52E-04 | 6.30E-05 | 2.52E-04 | 1.26E-04 |
| | $EDTA\ Na_2-H_2O$ | | 1.64E-02 | 4.10E-03 | 1.64E-02 | 8.20E-03 |
| | D-Pantothenic acid hemicalcium | | 5.46E-04 | 1.36E-04 | | |
| | Putrescine | | 4.97E-04 | 3.76E-04 | 5.03E-04 | 2.52E-04 |
| | Pyridoxal | | 5.46E-04 | 1.37E-04 | 5.46E-04 | 2.73E-04 |
| | D,L-Tocopherol Acetate | | 2.12E-05 | 5.30E-06 | 2.12E-05 | 1.06E-05 |
| | Thymidine | | 1.51E-03 | 1.13E-03 | 1.51E-03 | 7.54E-04 |
| | Vitamin A Acetate | | 3.04E-04 | 7.60E-05 | 3.04E-04 | 1.52E-04 |
| Organic acids/salts/esters | Na-Propionate | | 9.89E-01 | 2.47E-01 | 9.89E-01 | 4.95E-01 |
| | Linoleic acid | | 1.50E-04 | 4.49E-03 | 1.50E-04 | 8.97E-03 |
| | Methyl linoleate | | 1.70E-05 | 4.25E-06 | 1.70E-05 | 8.50E-06 |
| | Arachidonic acid | | 1.64E-02 | 4.10E-03 | 1.64E-02 | 8.20E-03 |
| Antibiotics | Penicillin G sodium | | 8.97E-02 | 8.75E-03 | 1.70E-01 | 8.50E-02 |
| Supplements | Sodium Bicarbonate | 1.43E+01 | 1.43E+01 | 1.92E+01 | 1.43E+01 | 2.02E+01 |
| | DL-6,8-Thioctic acid/Lipoic acid | 4.99E-04 | 4.99E-04 | 6.22E-04 | 5.10E-04 | 7.39E-04 |
| | Transferrin | 1.25E-04 | 1.25E-04 | 3.93E-03 | 5.00E-03 | 5.30E-03 |
| | Xanthine | | 2.20E-03 | 4.31E-03 | 1.50E-02 | 7.52E-03 |

TABLE 1-continued

Exemplary media formulations

| Category | Component | Concentration (mM)* | | | | |
|---|---|---|---|---|---|---|
| | | Medium 1 | Medium 2 | Medium 3 | Medium 4 | Medium 5 |
| | Insulin | | 8.61E−07 | 4.68E−04 | 1.00E−03 | 5.00E−04 |
| | Bovine serum albumin | | 3.76E−05 | 1.89E−03 | 3.76E−05 | 1.88E−05 |
| | hVEGF | | 1.00E−05 | 2.50E−06 | 1.00E−05 | 5.00E−06 |
| | FGF basic | | 1.00E−06 | 2.50E−07 | 1.00E−06 | 5.00E−07 |
| | Triiodothyronine | | 1.00E−07 | 2.79E−06 | 1.00E−07 | 5.00E−08 |
| | HEPES free acid | | 1.13E+01 | 6.58E+00 | | |
| | Tween 80 | | 1.50E−02 | 3.75E−03 | | |
| | Hypoxanthine | | 1.33E−02 | 3.32E−03 | | |
| | Uracil | | 2.70E−03 | 6.75E−04 | | |
| | Retinoic acid | | 9.99E−05 | 5.00E−05 | | |
| | EGF | | 5.00E−07 | 1.51E−05 | | |
| | Hydrocortisone | | 3.70E−05 | 3.43E−05 | | |
| | Ethanolamine | | 8.19E−06 | 1.27E−04 | | |
| | Glucagon | | 8.61E−07 | 2.15E−07 | 8.61E−07 | 4.31E−07 |
| | Bovine pituitary extract | | 1.00E−02 | 2.50E−03 | | |
| | Epinephrine | | 1.00E−03 | 2.50E−04 | | |
| | Phosphoryl-ethanolamine | | 5.00E−04 | 1.25E−04 | | |
| Trace Elements | Si | | 5.00E−02 | 1.25E−02 | | |
| | V | | 1.71E−06 | 1.25E−04 | 1.71E−06 | 8.55E−07 |
| | Mn | | 1.14E−06 | 2.53E−05 | 1.14E−06 | 5.71E−07 |
| | Mo | | 1.00E−04 | 2.50E−05 | | |
| | NiSO$_4$ | | 1.00E−04 | 2.50E−05 | | |
| | Sn | | 3.10E−06 | 1.33E−05 | 3.10E−06 | 1.55E−06 |
| | CuSO$_4$•5H$_2$O | 3.60E−07 | 3.60E−06 | 3.69E−06 | 3.60E−06 | 2.78E−06 |
| | GeO$_2$ | | 2.87E−06 | 7.18E−07 | 2.87E−06 | 1.44E−06 |
| | CrK(SO$_4$)$_2$ | | 2.47E−06 | 6.18E−07 | 2.47E−06 | 1.24E−06 |
| | AlCl$_3$ | | 6.00E−06 | 1.50E−06 | 6.00E−06 | 3.00E−06 |
| | MnCl$_2$ | | 1.14E−06 | 2.85E−07 | 1.14E−06 | 5.70E−07 |
| | KI | | 4.82E−07 | 1.21E−07 | 4.82E−07 | 2.41E−07 |
| | NiCl$_2$ | | 4.21E−07 | 1.05E−07 | 4.21E−07 | 2.11E−07 |
| | KBr | | 2.10E−07 | 5.25E−08 | 2.10E−07 | 1.05E−07 |
| | Na$_2$MoO$_4$ | | 2.07E−07 | 5.18E−08 | 2.07E−07 | 1.04E−07 |
| | Na$_2$SeO$_3$ | 3.80E−08 | 3.80E−08 | 1.24E−05 | 3.80E−08 | 1.60E−05 |
| | RbCl | | 3.31E−08 | 8.28E−09 | 3.31E−08 | 1.66E−08 |
| | AgCl | | 2.09E−08 | 5.23E−09 | 2.09E−08 | 1.05E−08 |
| | CoCl$_2$ | | 8.41E−09 | 2.10E−09 | 8.41E−09 | 4.21E−09 |

*Units for bovine pituitary extract are mg/ml and units for transferrin are g/L

In some examples, the pH of the disclosed media formulations is about 6.5-8.0, such as about pH 6.7-7.5, pH 6.8-7.2, pH 7.0-8.0, pH 7.3-7.6, pH 7.2-7.5, or pH 7.5-8.0. In some examples, the pH is about 6.5, 6.6, 6.7, 6.8, 6.9, 7.0, 7.1, 7.2, 7.3, 7.4, 7.5, 7.6, 7.7, 7.8, 7.9, or 8.0. In particular examples, the pH is about 7.4. One of ordinary skill in the art can select appropriate media pH (including pHs higher or lower than those described herein) for culture of particular cell types, tissues, and/or organs. One of ordinary skill in the art will also recognize that media pH may change over time during cell, tissue, or organ culture.

In some examples, the disclosed media formulations include glucose. Glucose (e.g., D-(+)-glucose) may be included in the medium when it is prepared, or the medium may be prepared without glucose, and glucose is added prior to use (for example, by the end user). In particular examples, glucose is included in the disclosed media at a final concentration of about 5-15 mM. In some non-limiting examples, glucose is included in Medium 1, Medium 2, or Medium 4 media (at preparation or added prior to use) at a final concentration of about 8.33 mM. In an additional non-limiting example, glucose is included in Medium 3 (at preparation or added prior to use) at a final concentration of about 14.5 mM. In a further non-limiting example, glucose is included in Medium 5 (at preparation or added prior to use) at a final concentration of about 12.9 mM.

In additional examples, the disclosed media include a pH indicator. The pH indicator (such as phenol red) may be included in the medium when it is prepared, or the medium may be prepared without the pH indicator and the indicator is added prior to use (for example, by the end user). In some examples, the pH indicator phenol red is included in the disclosed media at a final concentration of 0-25 M. In some non-limiting examples, phenol red is included in Medium 2 or Medium 4 (at preparation or added prior to use) at a final concentration of about 21.5 M. In other non-limiting examples, phenol red is included in Medium 3 or Medium 5 (at preparation or added prior to use) at a final concentration of about 0.8 M. In at least some examples, the medium does not include phenol red (for example, in some embodiments, Medium 1 does not include phenol red).

In additional examples, the disclosed media formulations also include one or more oxygen carriers. In some examples, an oxygen carrier is a hemoglobin-based oxygen carrier (such as hemoglobin or red blood cells or a composition including hemoglobin or red blood cells). In other examples, an oxygen carrier is a perfluorocarbon oxygen carrier (such as FLUORINERT™ fluid). Mixtures of hemoglobin-based oxygen carriers and perfluorocarbon oxygen carriers may also be utilized in the disclosed media.

Additional components can also be added to the disclosed media formulations. These additional components may include, but are not limited to, antibiotics (such as streptomycin, ampicillin, carbenicillin, gentamicin, kanamycin, neomycin, or polymyxin B), antimycotics (such as amphotericin B or nystatin), antioxidants (such as ascorbate), lipids (such as linolenic acid, oleic acid, or cholesterol), growth factors, trace elements, hormones, vitamins, or other components. Additional components, such as carriers may also be included in the media, for example to improve solubility in aqueous solutions (such as cyclodextrins to facilitate inclusion of lipids or lipid-soluble molecules in the disclosed aqueous solutions). In some examples, the media formulations may also include serum (such as fetal bovine serum or horse serum); however, in specific examples the media is serum-free (e.g., does not include any added or exogenous serum). In some examples, one or more test compounds (such as a drug candidate or other compound) may be added to the medium, for example, for functional, pharmacokinetic, toxicology, or other testing in a cell or organ culture or model.

III. Uses of Media Formulations

A. Cell, Tissue, or Organ Culture

The media formulations disclosed herein can be used in the culture of one or more (such as two, three, four, five, or more) cell types, tissues, and/or organs, for example in co-culture of one or more cell types, tissues, and/or organs. In particular non-limiting embodiments, the disclosed media formulations are used in the culture (such as maintenance, growth, viability, and/or function) of one or more "organs on a chip" or an "organism on a chip," such as devices that include cells and simulate tissues, organs, or organ systems (such as heart, lung, liver, and kidney). Such devices are described below and in International Patent Application No. PCT/US2015/052039, entitled "BIO-ASSESSMENT DEVICE AND METHOD OF MAKING THE DEVICE," filed on Sep. 24, 2015; and International Patent Application No. PCT/US2015/052043, entitled "DEVICES FOR FLUID MANAGEMENT," filed on Sep. 24, 2015; both of which are incorporated herein by reference in their entirety.

In particular embodiments of the disclosed methods, cells (such as one or more cell types, tissues, and/or organs) are contacted with one of the disclosed culture media under conditions suitable for the survival, growth, and/or function of the cells. In some examples, the cell(s), tissue(s), or organ(s) are contacted with the culture medium in a standard cell culture vessel (such as a dish, multiwell plate, or flask). In other examples, the cell(s), tissue(s), or organs(s) are contacted with the culture medium in a device (including, but not limited to, a bioreactor or a microfluidic device). In some examples, the culture medium is circulated between two or more chambers or organ devices (such as two or more fluidly connected chambers or organ devices) each containing one or more cell types. The disclosed media can also be used with any combination of cells, tissues, and/or organs in a single system.

In some embodiments of the disclosed methods, the cell culture (e.g., cells, tissues, or organs in contact with a disclosed medium) is maintained at a temperature suitable for the growth, maintenance, viability, and/or function of the cell(s), tissue(s), and/or organ(s). In some examples, the cell(s), tissue(s), and/or organs(s) are contacted with culture medium and incubated at a temperature of about 33-40° C. (such as about 33° C., 34° C., 35° C., 36° C., 37° C., 38° C., 39° C., or 40° C.). In other embodiments, the culture medium is pre-warmed to the desired temperature prior to contacting the cell(s), tissue(s), and/or organ(s) with the medium. One of ordinary skill in the art can select appropriate temperatures (including temperatures higher or lower than those described herein) for culture of particular cell types, tissues, and/or organs. One of ordinary skill in the art will also recognize that cultures can be maintained at higher or lower temperatures, for example for particular experimental conditions or due to equipment malfunction or operator error, for at least short periods of time without serious adverse consequences to the cells, tissues, or organs.

In some examples of the disclosed methods, the cell culture (e.g., cells, tissues, or organs in contact with a disclosed medium) is maintained in an environment (such as an incubator, chamber, or device) that includes a humidified atmosphere including about 5% $CO_2$ (such as about 3-7% $CO_2$). One of ordinary skill in the art will recognize that other environments can also be successfully used in the methods disclosed herein, and can select appropriate conditions based on the cell(s), tissue(s), and/or organ(s) being cultured and their use.

In one embodiment, the disclosed methods include contacting a culture including one or more of kidney, liver, heart, or lung cells with one of the media disclosed herein (such as Media 1-5). The cells may be in co-culture (e.g., in the same chamber or vessel), or may be in separate chambers or vessels that are fluidly interconnected. In some examples, the methods include contacting a culture including one or more (such as 2, 3, 4, 5, or more) fluidly connected chambers, vessels, tissues, organ devices, organs, or any combination thereof with one of the disclosed media. For example, the disclosed media may be circulated or perfused through the connected chambers, vessels, tissues, and/or organs, for example, in a circuit. In some examples, the exudates or secretions of one of the organs may provide one or more nutrients (e.g., glucose) or other necessary compounds for itself or one or more of the other cell types or organs, for example, through circulation of the media through a circuit among the organs. Thus, in some examples, the function of the one or more organs may supplement the media disclosed herein.

In some examples, any of Media 1-5 is used to culture heart, liver, lung, and kidney cells, for example, in a platform device including a heart organ, a liver organ, a lung organ, and a kidney organ. In other examples, Medium 4 or Medium 5 is used to culture heart and liver cells, for example, in a platform device including a heart organ and a liver organ. The cells, tissues, and/or organs are incubated under conditions sufficient to maintain the viability, growth, and/or function of the cultured cells, tissues, and/or organs, including, but not limited to, the conditions discussed above.

In some embodiments, the culture medium is circulated through (or recirculated through) two or more tissues or organ devices (for example, between two or more tissues or organ devices that are fluidly connected). In some examples, the disclosed media are utilized as the fluid in the platform devices described herein. In particular disclosed embodiments, one of the media disclosed herein (e.g., one of Media 1-5) is used in an organ perfusion system which controls fluid flow through a bio-assessment device or a platform including two or more fluidly coupled bio-assessment devices. In some examples, a medium disclosed herein is included in a reservoir of an integrated fluid management system of the perfusion system that is fluidly coupled to a bio-assessment device or platform device. The medium is pumped from the reservoir through the platform device or bio-assessment device. In some embodiments, the perfusion system continuously introduces fresh medium through the organ perfusion system and the bio-assessment device(s) through an inlet, and the medium passes out of the organ perfusion system and the bio-assessment device(s) through an outlet, for example to a waste container. In other embodiments, the perfusion system recirculates the medium through the organ perfusion system and the bio-assessment device(s). For example, the medium is passed through a circuit that continuously circulates medium through the perfusion system and bio-assessment device(s). In a recirculation circuit, fresh medium can be introduced either by replacing the recirculating medium during a single circulation, or fresh medium can be gradually introduced into the circuit at a set rate (e.g., 1-10 µl/minute). Other rates of introduction of fresh medium can be selected based on the desired time course for replacement, the volume of the system, the flow rate, and other system variables. The medium can be recirculated at a selected rate (e.g., 3 to 300 mL/min) in the recirculation circuit, or fresh media can be introduced (e.g., 0.5 mL to 50 mL/hr) from a fresh media circulation circuit to the bio-assessment devices.

B. Methods of Analyzing Response of Organs to Agents

In some embodiments, the platform devices can be used to analyze the response of one or more cells, tissues, organ constructs, or bio-assessment devices (such as 2 or more, 3 or more, 4 or more, such as a multi-organ construct or multi-organ system) to one or more agents, such as chemical or biological agents (referred to in some examples as test compounds or agents), including but not limited to drugs or drug candidates (e.g., pharmacological agents), toxins, infectious agents (such as bacteria, viruses, parasites, or fungi), nutritional supplements, nutraceuticals, and/or cosmetic products. Thus, in some examples, the methods disclosed herein are useful for toxicity testing, pharmacodynamics/pharmacokinetic testing, and/or efficacy testing of various agents. In particular examples, the disclosed methods can supplement or even replace in vivo testing of agents, for example in animal models, thus, decreasing drug development time. In particular, since the disclosed devices utilize human cells and their arrangement in organs and/or multi-organ systems, the methods can provide more data that are more physiologically relevant to humans than animal model systems.

In particular embodiments, a disclosed medium is circulated through the platform devices disclosed herein and one or more agents or substances is introduced to the platform device, for example, by adding the agent or substance to the medium during circulation through the platform. One or more effects of the agent(s) or substance(s) is measured at the system level, organ level, and/or cellular level. In some examples, the effects include molecular and biochemical effects, such as changes in gene expression/biomarkers (for example, presence and/or amount of proteins, nucleic acids (such as RNA or cDNA), or metabolic products), production and/or secretion of cellular products (such as enzymes, host defense molecules, surfactants, signaling molecules), or cell-cell interactions. In other examples, the effects include pharmacological or toxicological responses, such as drug metabolism (e.g., absorption, bioavailability, half-life, metabolism, tissue distribution, and/or clearance), changes in drug metabolism pathways (e.g., changes in metabolic and elimination pathways, such as cytochrome P450), or toxicity (such as cell death). In some examples, the effects of the agent(s) or compound(s) are measured by sampling the media at one or more time points after introducing the agent(s) or compound(s) to the platform and detecting presence or amount of one or more effects in the media (for example, after passing through a bio-assessment device, such as a lung device, liver device, heart device, or liver device).

In additional examples, the effects include physiological function of one or more tissues or organs. Organ-specific physiological functions may include production of enzymes, proteins, lipids, and/or xenosensors (liver); vesicle formation and cycling, beating cilia, and/or immunological/inflammatory functions (lung); glomerular filtration, urine production, concentration, or content, and/or renin release (kidney); beating rate or force of contractility, arrhythmia, and/or electrophysiology or action potentials (heart). Test compounds or agents may have one or more effects and their effects may overlap molecular/biochemical, pharmacological/toxicological, and physiological categories and/or may have effects on more than one organ construct. For example, test compounds or agents may have effects in one or more categories. Test compounds or agents may also have one or more effects in more than one organ construct. Furthermore, a particular effect of a test compounds or agents may be classified in more than one category. One of ordinary skill in the art can identify additional categories and/or effects that may be relevant to any particular test compound or agent.

In some embodiments, drugs and/or toxins disclosed herein can be tested to determine the anatomical and functional integrity of the bio-assessment device(s) used in the platform device. The platform device's pathophysiological fidelity also can be evaluated. Measurable indicators or biomarkers that are often predictive of functional consequences are used to assess the physiological state of the organ device. Moreover, multiple events will be probed at the organ, tissue, cellular and molecular level, enabling a comprehensive assessment of response. In some embodiments, a combination of on- and off-line methods can be used to monitor the bio-assessment device's physiological and biochemical signature responses. For example, the percent cell viability at different time points can be assessed and assigned to monitor tissue maturation and lifespan.

The anatomical and functional integrity of a bio-assessment device (or another device used with the platform device) is assessed by morphological (anatomical), physiological (e.g., glomerular filtration rate, or "GFR," vesicle formation, heart rate, etc.), metabolic characterization and molecular-level benchmark responses specific for each organ. In some embodiments, custom-designed, organ-specific gene array platforms (96 genes×96 conditions—HTP FLUIDIGM®) comprised of genes down-selected to represent a healthy and diseased tissue (gene profile in response to insult agent) are used for high through-put analysis of tissue/organ development, maturation and metabolic state. Embodiments of the array can also include genes that are more representative of a generalized toxicological response to realize the predictive aspects of the platform device and/or the bio-assessment device(s). In some embodiments, drug compounds with extensive human/animal exposure data can be used, such as FDA-approved toxic/non-toxic compounds, chemical threat agents, and pathogens. The well-known/measurable physiological responses and biomarker profiles of the drugs/toxins on human organs can then be used for comparison with the results obtained from using the disclosed platform devices and devices. Some compounds used herein are toxic to more than one organ, while others are efficacious in one and toxic to the other. Such compounds also can be used in the methods described herein. In exemplary embodiments, a threat agent-specific mini-chromosome maintenance protein inhibitor, e.g., ciprofloxacin after biological assessment exposure, can be used. To establish a predictive model of drug metabolism, the flow rate of the medium is maintained at rate that is sufficiently high to recapitulate nutrient/waste exchange as in the corresponding in vivo vasculature, but at the same time provide sufficient drug/media residence time in the perfused organ device, such as the lung organ device, to ensure a measurable drug metabolic response. A computational biology model can be used to evaluate the results. In some embodiments, doses and exposure times can be determined based upon literature data and/or the output from trial embodiments. For screening of non-linear responses, a plurality of concentrations, such as at least three concentrations, for each drug/chemical or can be used. In other embodiments, multiplicity of infection (MOI) analysis can be used for pathogens that are analyzed.

In some embodiments, the component to be analyzed (e.g., drug, toxin, pathogen, or the like) is introduced into the platform device or directly into one bio-assessment device. In some embodiments, the component to be analyzed is introduced into a platform device embodiment using a microformulator and is introduced in a manner that enables determination of both the dose-response and dose-timing associated with each observed effect. In other embodiments, the component to be analyzed is introduced into a particular bio-assessment device via an inlet of the bio-assessment device directly or via a fluid management device (for example, by including the compound in the medium introduced into the inlet or fluid management device). In some embodiments, the responses can be validated by correlation to corresponding human/animal pharmacokinetics (e.g., half-lives, tissue retention, distribution and clearance) and established signature responses. High fidelity validation endpoints that are sensitive, robust and generalizable to organ toxicity are determined, thus enabling predictive studies. In some embodiments, labeled drugs and chemical threat agents can be used to facilitate the ability to easily track their flow through and interactions with the organ device. For example, isotopic or fluorescent labeling of compounds enables rapid monitoring of the relative pharmacodynamics/pharmacokinetic efficiency of the bio-assessment device or of biochemical pathways.

In some embodiments, the platform devices disclosed herein can be used in combination with different detection methods to understand and validate the ability of the constructs and devices to respond to drugs and toxins. In particular embodiments, the platform devices and lung organ devices can be used in combination with ion mobility-mass spectrometry (IM-MS), which provides significant advantages over alternative MS strategies for complex biological studies by allowing the intricate characterization of the complex biomolecular profile through its unique modes of separation. In some embodiments, IM-MS first separates analytes, in the form of gas-phase ions, according to their orientationally averaged collision cross section with a neutral gas, which when performed under appropriate conditions correlates with molecular surface area. These separations can, in some embodiments, be analogous to gas-phase electrophoresis but in the gas-phase the timescale for separation is μseconds to mseconds, or nearly five orders of magnitude faster than condensed-phase separations of LC. Following IM separation, the ions are characterized by their mass using high speed MS analysis.

In some embodiments, ultra performance liquid chromatography (UPLC) can be used to quantify and/or identify compounds present in media used in the lung organ device and/or platform device. In some embodiments, UPLC can be used alone or in combination with the IM-MS techniques discussed above. In embodiments where UPLC and IM-MS are used together, they typically are operated in a multiplexed fashion to retain the temporal resolution of the microfluidics. Solely by way of example, a single 5 minute UPLC run can be duplexed to increase temporal resolution to less than 3 minutes with no sample loss (e.g., column 1 separates while column 2 is loaded). The microfluidic-UPLC-IM-MS platform can be used for online analysis, but with a delay of approximately 5 minutes between sample draw and data output. Such online techniques can be used to evaluate and/or monitor events at multiple points in the fluid path of a platform device nearly simultaneously.

Exemplary infectious agents that may be used in the disclosed methods (for example to assess the effects of an infectious agent or to screen for or test safety or efficacy of candidate treatments) include bacteria, such as *Francisella tularensis, Burkholderia* spp. (for example, *B. mallei, B. pseudomallei*), *Brucella* spp. (for example, *B. melitensis, B. abortus, B. suis*), *Yersina pestis, Bacillus anthracis, Mycobacterium tuberculosis, Legionella* spp. (for example, *L. pneumophila*), *Neisseria meningitidis, Streptococcus pneumoniae, Mycoplasma pneumoniae, Haemophilus influenzae* type B, or drug-resistant bacteria (such as drug-resistant *Staphylococcus aureus*, drug-resistant *Streptococcus pneumoniae*, for example, methicillin-resistant *Staphylococcus aureus*). Infectious agents that may be used in the disclosed methods also include viruses, such as influenza virus, hepatitis virus (such as hepatitis A, hepatitis B, or hepatitis C), human immunodeficiency virus, respiratory syncytial virus, polyoma virus, cytomegalovirus, human papilloma virus, flavivirus (for example, Dengue virus, West Nile virus, St. Louis encephalitis virus, Japanese encephalitis virus, tick-borne encephalitis virus), togavirus (for example, rubella, Western equine encephalitis, Eastern equine encephalitis, Venezuelan equine encephalitis virus), filoviruses (for example, Ebola virus, Marburg virus), enteroviruses, poliovirus, and smallpox virus. In other examples, infectious agents that may be used in the disclosed methods include fungi (such as *Candida, Aspergillus, Blastomyces, Coccidioides, Cryptococcus, Histoplasma, Pneumocystis, Sporothrix, Exserohilum*) or parasites (such as *Plasmodium, Trypanosoma, Toxoplasma, Leishmania, Cryptosporidium, Giardia, Trichinella*). One of ordinary skill in the art can identify other infectious agents that can be used with the methods and devices disclosed herein.

In some examples, the disclosed methods include testing of chemical agents (such as chemical warfare agents), for example, to assess the effects of a chemical agent or to screen for or test safety or efficacy of candidate treatments (such as medical countermeasures, MCMs). Exemplary chemical agents include tear agents (for example, a-chlorotoluene, benzyl bromide, bromoacetone, bromobenzylcyanide, capsaicin, chloracetophenone, chloromethyl chloroformate, dibenzoxazepine (CR), ethyl iodoacetate, ortho-chlorobenzylidene malonitrile, trichloromethyl chloroformate, xylyl bromide), vomiting agents (adamsite, diphenylchloroarsine, diphenylcyanoarsine), or malodorants. Chemical agents also include psychological agents (for example, 3-quinuclidinyl benzilate, phencyclidine, lysergic acid diethylamide), nitrogen mustards (such as bis(2-chloroethyl)ethylamine, bis(2-chloroethyl)methylamine, tris(2-chloroethyl)amine), sulfur mustards (for example, 1,2-bis (2-chloroethylthio) ethane, 1,3-bis(2-chloroethylthio)-n-propane, 1,3-bis(2-chloroethylthio)-n-butane, 1,5-bis(2-chloroethylthio)-n-pentane, 2-chloroethylchloromethylsulfide, bis(2-chloroethyl) sulfide, bis(2-chloroethylthio) methane, bis(2-chloroethylthiomethyl) ether, bis(2-chloroethylthioethyl) ether), arsenicals (such as ethyldichloroarsine, methyldichloroarsine, phenyldichloroarsine, 2-chlorovinyldichloroarsine), phosgene oxime, cyanogen chloride, hydrogen cyanide, arsine, chlorine, chloropicrin, diphosgene, phosgene. Additional exemplary chemical agents also include nerve agents, for example, sarin, soman, tabun, cyclosarin, Novicok agents, GV, VE, VG, VM, VX, saxitoxin). One of ordinary skill in the art can identify additional chemical agents that could be used with the devices and methods disclosed herein.

In additional examples, the disclosed methods include testing of toxins (which may include chemical agents discussed above), for example, to assess the effects of a toxin or to screen for or to test safety or efficacy of candidate treatments. Toxins include biological toxins (toxins of biological origin) as well as environmental toxins, such as industrial pollutants or synthetic toxic substances. Exemplary toxins include but are not limited to ricin, botulinum toxin, tetrodotoxin, chlorotoxin, conotoxin, tetanus toxin, bungarotoxin, dendrotoxin, batrachotoxin, curare, pertussis toxin, diphtheria toxin, crotamine, or other reptile or insect venoms. Additional exemplary toxins include pesticides (such as organophosphates, carbamates, organochlorines, neonicotinoids, or pyrethroids), herbicides (such as glyphosate, atrazine, 2,4-D, dicamba, trifluralin, pendimethalin, metolachlor), heavy metals (such as lead, mercury, chromium, cadmium, arsenic), volatile organic compounds (such as benzene, formaldehyde, toluene, perchlroethylene), asbestos, bis-phenol A, and polychlorinated biphenyls (PCBs). One of ordinary skill in the art can identify additional toxins that could be used with the devices and methods disclosed herein.

Exemplary compounds or agents also include, but are not limited to, peptides, such as soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds, for example, shRNA, siRNA, sgRNA).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds. Exemplary libraries are available from the NIH Molecular Libraries Program (Molecular Libraries Small Molecule Repository), the NIH Developmental Therapeutics Program compound sets, GlaxoSmithKline, Sigma-Aldrich, Microsource Discovery Systems, ChemBridge, Selleck-Chem, DNA2.0, AbCheck, GenScript, Thermo Fisher Scientific, GE Dharmacon, Cellecta, Charles River, Phoenix Pharmaceuticals, the EPA ToxCast™ library, and the World Toxin Bank. One of ordinary skill in the art can identify suitable compounds and/or libraries for use in the methods disclosed herein.

In some embodiments one or more of the disclosed media (such as Medium 1, Medium 2, Medium 3, Medium 4, or Medium 5) is utilized as the fluid component in a platform device used to facilitate coupling and operation of a plurality of bio-assessment devices (such as 2, 3, 4, 5, or more bio-assessment devices) and their corresponding components. In some embodiments, the platform device can be used to control interactions between a plurality of bio-assessment devices and thereby couple such devices in a manner that allows fluid communication between the bio-assessment devices. In particular disclosed embodiments, the platform device is used to facilitate biological analysis using the plurality of bio-assessment devices and can thereby be used to evaluate the effects of biomedical drugs and/or toxic substances on particular organs of the body without having to administer the drugs in vivo. The platform device can be used in combination with a variety of different bio-assessment devices, each of which is a biomechanical construct of its corresponding human organ counterpart. For example, bio-assessment devices that can be used with the disclosed platform devices include, but are not limited to, lung devices, heart devices, liver devices, kidney devices, and the like. An exemplary lung bio-assessment device is disclosed in International Patent Application No. PCT/US2015/052039, entitled "BIO-ASSESSMENT DEVICE AND METHOD OF MAKING THE DEVICE," filed on Sep. 24, 2015. Additional bio-assessment devices, such as liver devices, kidney devices, and heart devices are described in U.S. Patent Application Publication No. 2014/0356849, and International Application Publication No. WO 2014/081840, each of which is incorporated herein by reference.

In particular disclosed embodiments, the platform device comprises a plurality of components that together function to control each bio-assessment device, evaluate operation of each bio-assessment device, and/or control and evaluate the effects of various substances administered into the integrated system. The platform device can comprise a combination of organ sensing and control instrumentation, such as, but not limited to, one or more of an organ perfusion system, an air supply, a fresh media circuit, a recirculation circuit, a microformulator, pump(s) (e.g., rotary peristaltic pump(s)), valve(s) (e.g., rotary planar valve(s)), an integrated multi-organ perfusion controller and/or a microclinical analyzer, multichannel potentiostat(s), electrode(s), and any combination of two or more thereof.

In some embodiments, the platform device is configured to fluidly couple a plurality of bio-assessment devices by including certain of the components described above. In some embodiments, the plurality of bio-assessment devices includes, but is not limited to, a lung device, a heart device, a liver device, a kidney device, or other organ devices (such as a vascular device or a neuronal device). The organ devices may be connected in parallel, in series, or a in a configuration combining parallel and serial relationships between the organ devices. In one exemplary embodiment, a heart device (which may include left heart and right heart components) is fluidly coupled to a lung device, a liver device, and a kidney device. One or more of the heart, lung, liver, and kidney devices are fluidly coupled to a fluid transport system including one or more reservoirs, fluidly coupled to fluid inlets and outlets of the organ device(s). In some embodiments, the fluid transport system can comprise a perfusion system as described in more detail herein.

In one exemplary embodiment, a platform device comprises an air supply component (e.g., a ventilator, an air tank, or the like) coupled to a lung organ device, which in turn is fluidly coupled to a heart device, such as a single heart device or a left heart device and a right heart device. In some embodiments, a singular heart device (or a left heart device) is fluidly coupled to a fresh media circuit, which comprises a separate reservoir containing arterial system fluids and/or other nutrients. The fresh media circuit is further fluidly coupled (directly or indirectly) to the fluid inlets of the liver device and the lung organ device, as well as the fluid inlets of a gut microformulator, a kidney device, a multi-organ perfusion controller, a missing organ microformulator, or a combination thereof. The singular heart device (or a right heart device) can be fluidly coupled to a recirculation circuit. The recirculation circuit can comprise a reservoir suitable for accepting fluids delivered from the various bio-assessment devices of the platform device. The recirculation circuit is further fluidly coupled (directly or indirectly) to the lung organ device, a liver device, the kidney device, the multi-organ perfusion controller, a missing organ microformulator, or a combination thereof. Exemplary platform device configurations are provided in U.S. Patent Application Publication No. 2014/0356849, and International Application Publication No. WO 2014/081840, both of which are incorporated herein by reference. Any suitable configuration can be used to couple the bio-assessment devices of the platform device. For example, the bio-assessment devices, including the lung organ devices disclosed herein can be fluidly coupled in parallel, wherein fluid management devices, such as those disclosed in International Patent Application No. PCT/US2015/052043, entitled "DEVICES FOR FLUID MANAGEMENT," filed on Sep. 24, 2015, provide the ability to control each of the bio-assessment devices present in the platform. In yet additional embodiments, one or more of the bio-assessment devices are fluidly connected in parallel, while one or more bio-assessment devices are connected in series. In such embodiments, the serially connected bio-assessment device(s) is coupled parallel to the bio-assessment devices that are connected in parallel. For example, a gastrointestinal organ device (or a missing organ microformulator) can be positioned upstream from a liver organ device, and both of these organ devices can be coupled in parallel to a kidney organ device and one or more of a lung organ device and a heart device. In another embodiment, a heart device can be fluidly coupled in series with a lung organ device, wherein the lung device is fluidly coupled in series to a single heart device, or fluidly coupled in series between both a right heart device and a left heart device. In some embodiments, the platform device provides the ability to bypass one or more bio-assessment devices within the platform device, for example for maintenance, sample collection, or to study the effects of removing one bio-assessment device from the system.

Figure 9:
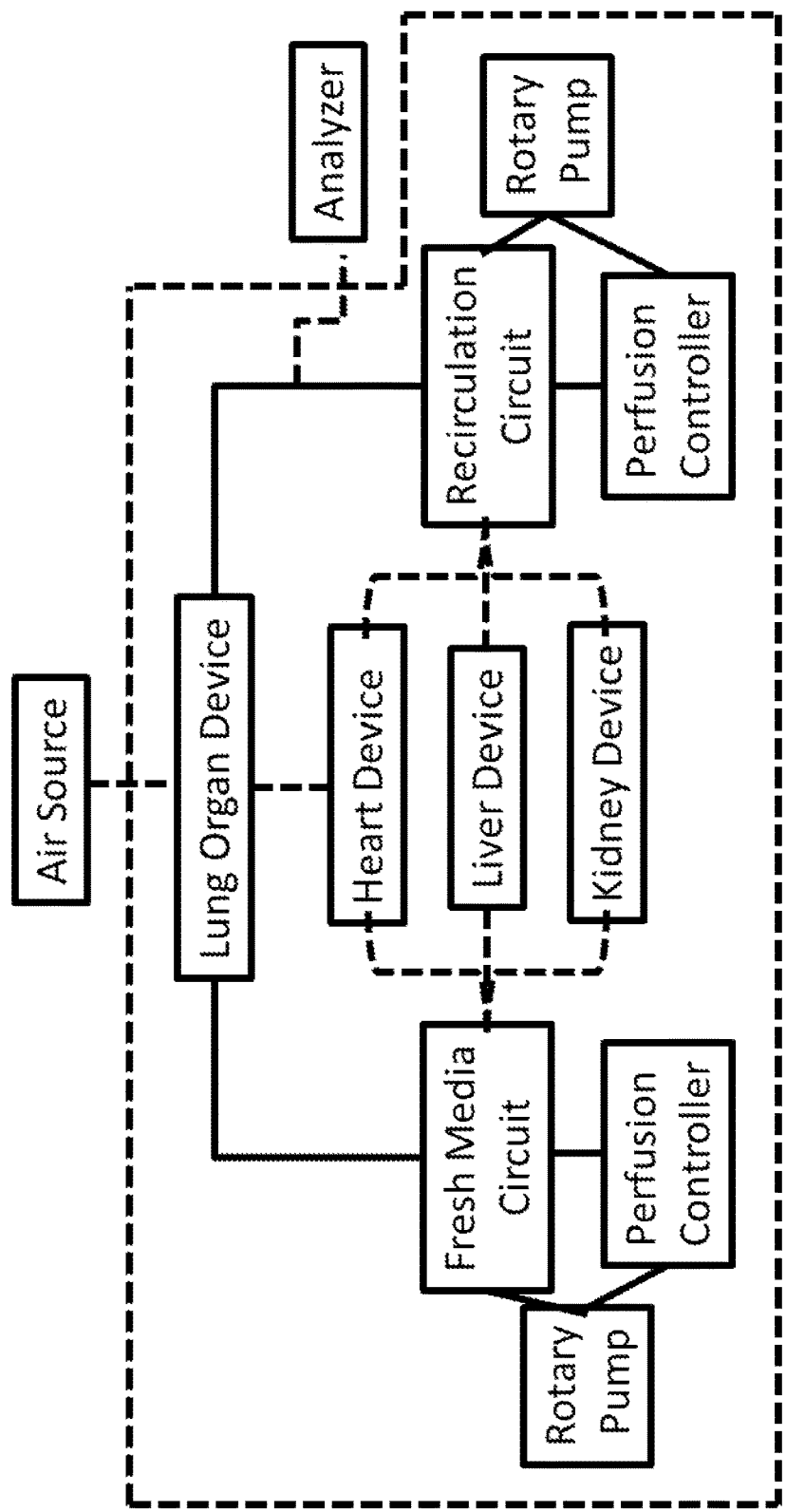
FIG. 9 is a schematic diagram of a representative embodiment of a platform device comprising a plurality of bio-assessment devices that can be utilized with the media described herein.

FIG. 9 is a schematic illustration of an exemplary platform device configuration comprising a lung organ device and a plurality of other optional bio-assessment devices. As illustrated in FIG. 9, an exemplary platform device embodiment can comprise an air source that can be coupled to a lung organ device, which in turn can be fluidly coupled to a heart device. The heart device and the lung organ device are coupled to a fresh media circuit, which can be further fluidly coupled to a liver device and a kidney device. The fresh media circuit also can be coupled to a multi-organ perfusion controller and one or more rotary pumps. As illustrated in FIG. 9, the lung organ device, and any other optional bio-assessment devices, can be coupled to a recirculation circuit, which can also be coupled to a perfusion controller and one or more rotary pumps. The platform device can also optionally include an analyzer which can be in fluid communication with the recirculation circuit, the perfusion system, and/or any of the bio-assessment devices. The embodiment illustrated in FIG. 9 is not intended to be limiting, but instead is provided as a representative embodiment to illustrate one possible way in which the components can be arranged using embodiments of the disclosed platform.

In particular disclosed embodiments, an organ perfusion system is used to control fluid flow (such as flow of one of the media disclosed herein) throughout the platform device and the bio-assessment devices used with the platform device. In some embodiments, the perfusion system comprises a perfusion controller comprising a fluid management system and one or more pumps capable of delivering perfusion fluids, nutrients, and/or biological media. In some embodiments, the organ perfusion system comprises a recirculation circuit (for example, a circuit that continuously circulates medium through the perfusion system) and a fresh media circulation circuit (for example, a circuit that introduces fresh medium into the perfusion system). The perfusion system can comprise one or more pumps that provide media recirculation (e.g., 3 to 300 mL/min) in the recirculation circuit, and fresh media (e.g., 0.5 mL to 50 mL/hr) from the fresh media circulation circuit to the bio-assessment devices. In some embodiments, the perfusion controller of the perfusion system can operate in different modes, such as a bypass control mode, a serial perfusion mode, and an organ replacement perfusion mode. In an embodiment of a bypass control mode, the perfusion controller is used to allow medium (such as blood surrogate or universal medium) to bypass a bio-assessment device, for example so that a different medium can be delivered to the bio-assessment device. In an embodiment of a serial perfusion mode, a bio-assessment device, which is in a serial configuration with one or more bio-assessment devices, is perfused in series with the other bio-assessment devices. In an embodiment of an organ replacement perfusion mode, a bio-assessment device is removed from the platform device and therefore isolated from other bio-assessment devices of the platform device. Flow through the platform device is maintained by utilizing fluid management devices of the bio-assessment devices. A component for analysis, such as a drug, toxin, or other compounds or agents, can then be introduced into the isolated bio-assessment device for evaluation and analysis. In this manner, the effect of one or more compounds on the particular bio-assessment device can be evaluated without exposing other bio-assessment devices to the compound(s). The perfusion system can be fluidly coupled to other components of the platform device and/or the bio-assessment devices or components of the bio-assessment devices. In some embodiments, the perfusion system is fluidly coupled to a recirculation circuit (e.g., a venous system) via one or more inlets and/or a fresh media circuit (e.g., an arterial system) via one or more outlets. In additional embodiments, the perfusion system is fluidly coupled directly to the lung organ device disclosed herein. The perfusion system also can be directly coupled to one or more of a heart device, a liver device, or a kidney device. In yet other embodiments, the perfusion system can be fluidly coupled to a fluid management device that is further fluidly coupled to a bio-assessment device. The perfusion system also can be fluidly coupled to one or more microformulators included in the platform device.

In some embodiments, a computer can be used with the organ perfusion system to regulate variables such as temperature, air, $O_2$, $CO_2$, fluid flow rate, and perfusion pressure. The on-board computer also records culture variables (e.g., pH and $O_2$), and can be used to externally control the perfusion controller and thereby fluid flow into and out of the platform device (and thereby the plurality of bio-assessment devices).

In some embodiments, the platform device can further comprise one or more microformulators. The microformulators can be used to prepare and facilitate precise delivery of desired amounts of perfusion media to the platform device. The microformulators can comprise a plurality of pneumatic microfluidic valves and solenoid valves to deliver perfusate to the bio-assessment devices from the organ perfusion system. In some embodiments, the microformulator is used to deliver nutrients, metabolites, hormones, paracrine signals, and/or drugs or agents to be analyzed using the platform device to one or more bio-assessment devices. In some embodiments, the microformulator is used to deliver nutrients, metabolites, hormones, paracrine signals, and/or drugs or agents being analyzed with the platform device that would be provided by organ devices not included for use in the platform (e.g., a device other than a heart device, lung device, kidney device, or liver device). In such embodiments, the microformulator can be referred to herein as a "missing organ" microformulator. Solely by way of example, a missing organ microformulator can be used in place of endocrine organs, the gut, and the brain and therefore can provide biological components, such as fatty acids and other biologically relevant molecular species. The microformulators can be used to provide controlled additions of nutrients, metabolites, hormones, paracrine signals, and/or drugs or agents to media passed through the platform device and the bio-assessment devices (e.g., fluids, such as blood surrogate, air, and other biological media). A combination of microformulators for use with a bio-assessment device and missing organ microformulators can be used in the platform device. In some embodiments, an individual microformulator can be positioned upstream of each bio-assessment device to provide media supplements specifically required by a particular bio-assessment device. If specific molecules produced by or introduced into a particular bio-assessment device are toxic to another bio-assessment device, a size exclusion filter or an antibody-based affinity separator can be used in conjunction with the microformulator and the bio-assessment device to remove the toxic molecules from the perfusion stream that is fluidly coupled to that bio-assessment device. In particular disclosed embodiments, a microformulator can be used in combination with a countercurrent dialysis system to reduce the local concentration of specific molecules in media passing through the platform device and bio-assessment devices. Representative embodiments of a microformulator are described in U.S. Patent Application Publication No. 2014/0356849 and WO 2014/081840.

The platform devices can comprise one or more pumps (such as peristaltic pumps) that are used to facilitate flow of media through the platform device and the various bio-assessment devices used with the platform. The pumps can be miniaturized, such as micropumps or nanopumps. The pumps are optionally used in combination with one or more of the microformulators. In some examples, the pumps are rotary peristaltic pumps such as those described in PCT Publication No. WO/2012/048261, which is incorporated herein by reference, as well as U.S. Patent Application Publication No. 2014/0356849. The pumps can be used in combination with valves (such as rotary planar valves), which also are described in PCT Publication No. WO/2012/048261 and U.S. Patent Application Publication No. 2014/0356849.

In additional embodiments, the platform devices can comprise integrated fluid management devices capable of managing fluid flow into the bio-assessment devices. The integrated fluid management devices a fluid management device including one or more channel substrates comprising one or more channels and a connection substrate comprising one or more inlets and/or outlets; a valving system comprising one or more valves positioned off-plane of the connection substrate and fluidly coupled to the one or more channels; and a reservoir including one or more chambers for housing a fluid and one or more ports for delivering fluid to or from the one or more chambers. Exemplary fluid management devices are discussed below and disclosed in International Patent Application No. PCT/US2015/052043 entitled "DEVICES FOR FLUID MANAGEMENT," filed on Sep. 24, 2015, incorporated herein by reference.

In some embodiments, the fluid management devices include planar substrate devices comprising an optional base substrate, one or more channel substrates, and a connection substrate. In some embodiments, two or more channel substrates can be included in the fluid management device. In yet other embodiments, no channel substrates are needed and only a base substrate and connection substrate are provided. In yet other embodiments only a connection substrate is needed. The number of base and/or channel substrates used in the fluid management device can be modified according to the type of reactor to which it is fluidly coupled. Solely by way of example, a plurality of channel substrates (e.g., two or more, three or more, four or more, and so on) can be used to provide an increased number of flow channels that can be fluidly connected to one or more bio-assessment devices. The substrates of the fluid management device can be made from a material suitable for laser ablation channel formation. In some embodiments, the substrates are formed from a biocompatible material. In some exemplary embodiments, the substrates are formed from polymeric materials selected from, but not limited to polydimethylsiloxane (PDMS), and/or acrylic or polycarbonate materials. In some embodiments, the substrates can have the same thickness, or progressively increasing thicknesses. Substrate thicknesses can range from 1 μm to 2 mm, such as 1 μm to 1 mm, or 1 μm to 0.5 mm. In exemplary embodiments, the substrate thickness can be selected from 1 μm, 100 μm, 200 μm, 0.2 mm, 0.5 mm, and 1 mm.

In particular disclosed embodiments, the base substrate and/or optional channel substrates are fabricated to comprise flow channels that are fluidly coupled to provide a multi-layer channel network. In some embodiments, some or all of the channels can be fluidly coupled together. The channels can be micro-sized channels (e.g., microchannels), nano-sized channels (e.g., nanochannels), large-sized channels, or combinations thereof. The term "microchannels," as used herein, is understood to refer to channels having dimensions less than 1 mm and greater than or equal to 1 μm. The term "nanochannels," as used herein, is understood to refer to channels having dimensions less than 1 μm and greater than or equal to 1 nm. In yet other embodiments, the channels can be large-sized channels having dimensions less than 10 mm and greater than or equal to 1 mm. The channel dimensions can be modified according to the reactor to which the fluid management device is coupled. For example, fluid management devices comprising large channels (e.g., channels having dimensions less than 10 mm channels and greater than or equal to 1 mm) can be coupled to high-volume reactors (e.g., 1 or more liters). In yet other examples, fluid management devices comprising microchannels and/or nanochannels can be coupled to lower-volume reactors (e.g., under 1 liter, such as microliter-, nanoliter-, or milliliter-scale reactors). In some exemplary embodiments, microchannels having dimensions of 2 µm to 10 µm can be used, such as 5 µm to 10 µm. Each substrate can comprise a plurality of channels and each substrate can have a different number of channels. The channels of each substrate can have the same or different dimensions. In some embodiments, the channels can have configurations that differ with each substrate. In some embodiments, the substrates include a plurality of channels that are fluidly coupled to one another when the device is assembled by stacking the substrates on top of each other.

The substrates also can comprise one or more inlets, outlets, ports or combinations thereof. The connection substrate of the fluid management device comprises inlets and outlets through which fluids can be delivered to and from the fluid management device. Certain inlets and outlets are coupled to ports that extend from the planar surface of the connection substrate and allow for physical connection between tubes and the connection substrate. Using these inlets and outlets, fluids are delivered between the fluid management device and the reactor(s), reservoirs, and/or pumps (e.g., peristaltic pumps) to which the fluid management device is fluidly coupled. The connection substrate also comprises two or more inlets that are fluidly coupled to a valving system connected to the fluid management device to control flow of fluids through the fluid management device and the various components connected thereto. In some embodiments, the feed holes that are fluidly coupled to the valves are aligned along one side of the connection substrate; however, other suitable alternative configurations can be used.

Figure 10:
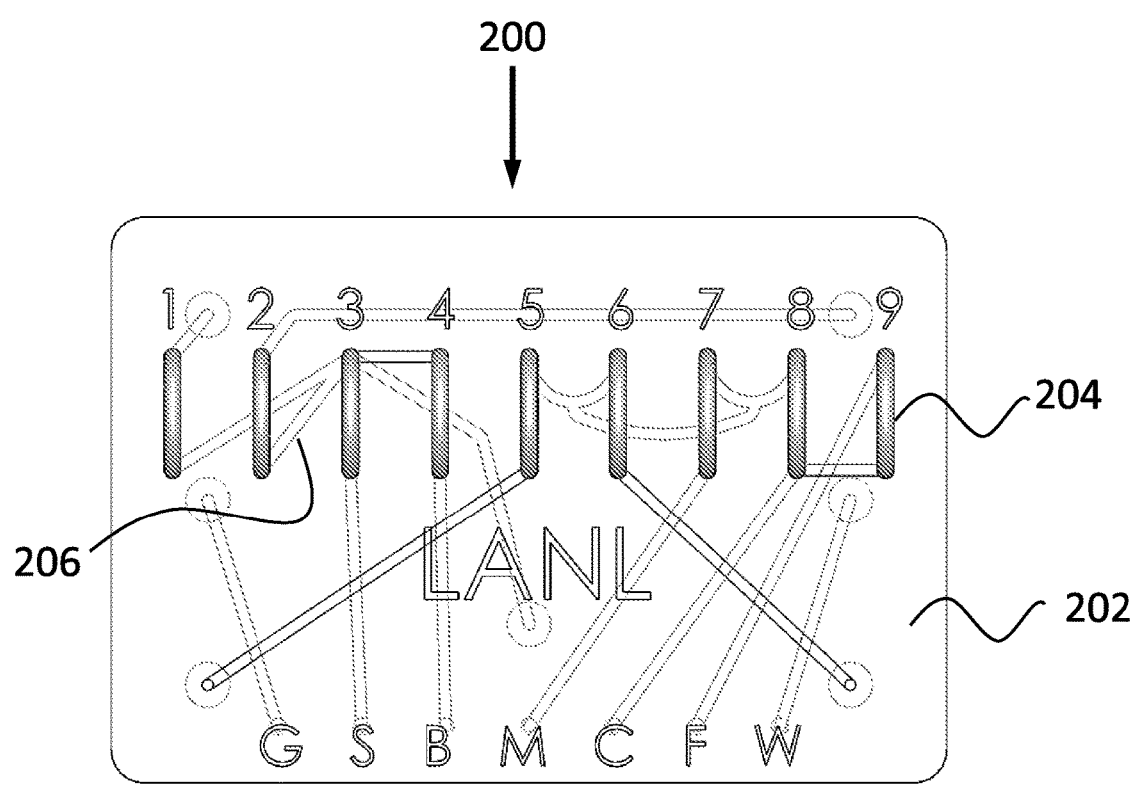
FIG. 10 is a top plan view of an exemplary constructed fluid management device.
Figure 11:
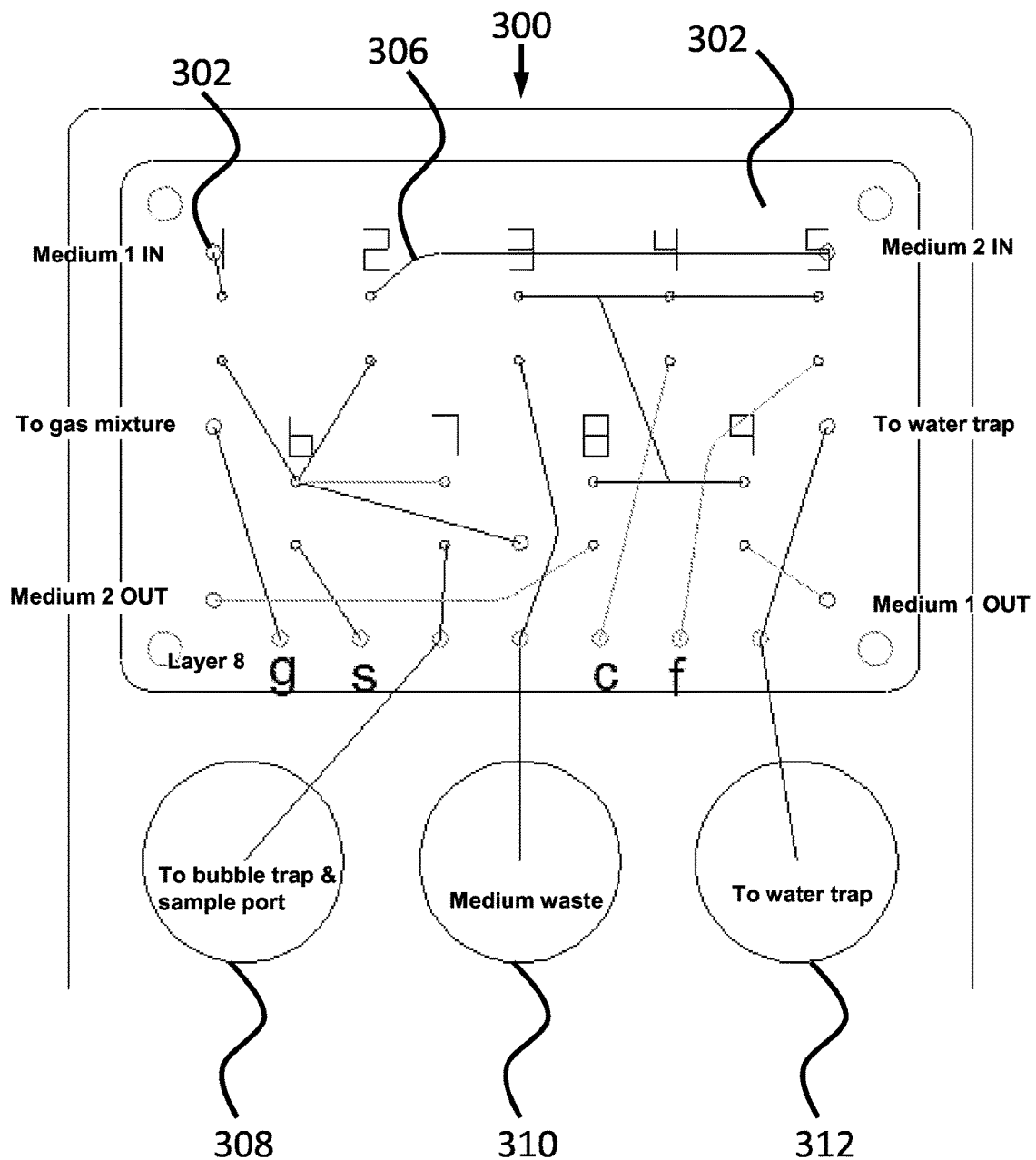
FIG. 11 is a top plan view of an exemplary substrate comprising a plurality of channels and inlets/outlets for delivering fluids through the fluid management device, and further illustrating reservoir chambers that can be coupled to the fluid management device.

FIG. 10 illustrates a top plan view of an exemplary connection substrate embodiment 202 of a fluid management device. As illustrated in FIG. 10, a plurality of arch valves 204 can be used to control flow into and out of flow channels 206 of the fluid management device 202. FIG. 11 illustrates exemplary channel configurations that can be used. As illustrated in FIG. 11, multiple channels 306 can be fluidly coupled to multiple inlet/outlets 304 present on substrate 302 of the fluid management device 300. Connections, such as tube connections can be used to connect the fluid management device 300 to chambers 308, 310, and 312 of a reservoir (not illustrated) that is positioned adjacent to the fluid management device.

The fluid management devices comprise unique valving systems that facilitate delivering the various fluids delivered through the fluid management device to and from the reactor, the reservoir, and one or more pumps. The valving systems described herein provide the ability to modify connections and/or control flow into the channel network of the fluid management device without having to disassemble the fluid management device to access the channel network of a base substrate (and/or optional channel substrates). Furthermore, fluid flow through the fluid management device and the bio-assessment device(s) can be controlled via simple manipulation of the valves of the valving system, such as by deforming (e.g., pinching) the valves closed and then allowing the valves to reform (e.g., by unpinching) to allow flow to continue.

In some embodiments, the valves are arch valves that extend off-plane from the planar substrate and are connected to at least two inlets of the connection substrate. In some embodiments, the valves comprise a flexible material, such as tubing material known to those of ordinary skill in the art. In some embodiments, the flexible material is biocompatible. In some embodiments, the valves can be controlled using mechanical, magnetic, and/or pneumatic systems. In exemplary embodiments, the valves are arch valves that can be used in combination with other separate valves that facilitate control of the arch valves, such as pinch valves, latching solenoid valves, or combinations thereof. In some embodiments, these valves can be controlled manually or they can be automated. The valves can be connected to the fluid management device by ports that are coupled to the surface of the connection substrate. These ports are associated with inlets of the connection substrate and therefore are fluidly coupled to the channels of the integrated channel network.

The integrated fluid management devices also include reservoirs that are used in combination with the fluid management devices described herein. In some embodiments, the reservoirs are used to store fluids that are first delivered to the fluid management device and then are delivered to a platform device. The reservoirs can be fabricated as an integrated component comprising multiple reservoirs (such as one or more fluid storage reservoirs and/or one or more waste reservoirs). This capability provides an advantage over conventional reservoirs, which typically are separated/isolated chambers that each requires a separate tubing set-up to facilitate fluid delivery. Separate chambers can cause issues with set-up, are not user-friendly, and can require extraneous space and components that increase operation and fabrication costs. In contrast, the presently disclosed reservoirs are made using durable, cost-efficient materials, can be easily removed from (or integrated with) the reactor set-up, and are compact. In exemplary embodiments, a reservoir comprises a chamber that functions as a bubble trap, a chamber that functions as a water trap, a feed chamber, and a waste chamber. Each chamber can be configured to comprise a readable scale on the chamber wall. The readable scale can be used to visually determine the amount of fluid present in the chambers of the reservoir. In yet additional embodiments, one or more chambers of the reservoirs can be configured to comprise membranes, such as gas permeable membranes to accommodate diffusion of gases produced by or introduced into the reactor without permitting fluid to pass through the membrane. The chambers also can comprise sensors that can be used to detect changes in, for example, fluid level, pH, gas concentration, and the like.

The device components described herein can be integrated to form an integrated fluid management device. In particular disclosed embodiments, the fluid management device is fluidly coupled to a reservoir via one or more inlets present on the connection substrate. The inlets of the fluid management device can comprise ports to which tubes can be connected, which are also connected to inlets and/or outlets and ports present on the reservoir. The fluid management device can also be coupled to one or more of the valve systems disclosed herein to form an integrated fluid management device. The integrated fluid management device is fluidly coupled to a bio-assessment device (such as a bio-assessment device included in a platform described herein) through ports which deliver fluids from the integrated channel network of the fluid management device to the bio-assessment device.

The platform devices disclosed herein also can comprise analyzers or sensors capable of detecting properties and the chemical make-up of fluids passed through the platform device, such as effluent exiting a bio-assessment device or perfusate entering a bio-assessment device. In some embodiments, the analyzers or sensors are integrated with the perfusion controller to form one singular component, and in other embodiments they are separate components. In some embodiments, the analyzers, sensors, and perfusion controllers can be used to prevent issues associated with calibration and fouling of in-line electrochemical sensors, to isolate the bio-assessment devices of the platform for seeding, diagnosis, and/or treatment protocols, for inter-bio-assessment device media balancing and shunting, and to provide additional local perfusion or gas exchange. In other examples, the analyzers or sensors are used to determine the functioning of one or more of the bio-assessment devices or the effect of one or more introduced compounds, for example on metabolism, secretion, gene expression, and so on. Analyzers can include one or more of devices or instrumentation for liquid chromatography (for example, high performance liquid chromatography or ultra performance liquid chromatography), mass spectrometry (MS; such as MS-MS, gas chromatography-MS, ion mobility-MS), or a combination thereof. In one example, the analyzer includes instrumentation for ultra performance liquid chromatography-ion mobility-MS.

In some embodiments of the disclosed platform devices, multichannel potentiostats can be used to measure dynamic changes in glucose, lactate, oxygen, and pH in cells and media used in the bio-assessment devices. Embodiments of a multichannel potentiostat that can be used with the disclosed platform devices are described, for example, in U.S. Patent Application Publication No. 2014/0356849.

EXAMPLES

The following examples are illustrative of disclosed embodiments. In light of this disclosure, those of skill in the art will recognize that variations of these examples and other examples of the disclosed technology would be possible without undue experimentation.

Example 1

Methods

Cells were initially expanded and cultured according to the vendor's instructions. At 80-90% confluence, cells were switched for 24 hours to 50% vendor's media and 50% test media. Media was changed at 24 hours to 100% test media, unless otherwise indicated. Cells were obtained from the following vendors: Human iPSC-derived Cardiomyocytes (Cor4U), Axiogenesis, Cologne, Germany; Human Primary Lung Microvascular Endothelial Cells, (HLMVECs) Cell Applications, San Diego, Calif.; Human Primary alveolar Type 1 and 2 origin (AT1, AT2), Celprogen, Torrance, Calif.; Human Frozen Primary Liver cells (PHH), TRL, Research Triangle Park, N.C.; Human Primary Bronchial/Tracheal Epithelial Cells (HBTEC) and Human Primary Mixed Renal Epithelial (NHRE), Lifeline Cell Technology, Frederick, Md.

Real-Time PCR was performed with Applied Biosystems Cells to CT kit and pre-developed assay reagents. The LDH and WST assays (Roche) were performed according to package inserts. Images were taken on the EVOS microscope (Applied Biosystems).

Custom media formulations were designed based on published formulas currently in use for organ cultures of heart, lung, liver, and kidney. Custom software was utilized to assist in developing media formulations. Osmolarity, pH and buffer capacity were calculated for the new formulations using this software. Heparmed was obtained from Biochrom AG (now Millipore). Custom media was manufactured by Lifeline Cell Technology.

Example 2

Initial Studies

Primary alveolar cells (AT1 or AT2) were grown for 14 days in different commercial media with or without serum. Gene expression was evaluated after 14 days. These cells are known to de-differentiate in culture. One AT2 marker, SPA (a surfactant protein), returned when serum was removed from the culture (Table 2). These data suggest that serum might be detrimental to maintaining the cells in a differentiated state, and that AT1 and AT2 cells could be sustained in serum-free media.

TABLE 2

Gene expression in AT1 and AT2 cells following 14 days of culture in medium with or without serum.

| | GABAP | KRT18 | Vim | Podoplanin | SPA1 |
|---|---|---|---|---|---|
| AT1 ctrl media | + | + | + | − | − |
| AT1 no serum | + | + | + | − | − |
| AT2 ctrl media | + | + | + | − | − |
| AT2 no serum | + | + | + | − | + |

Figure 2:
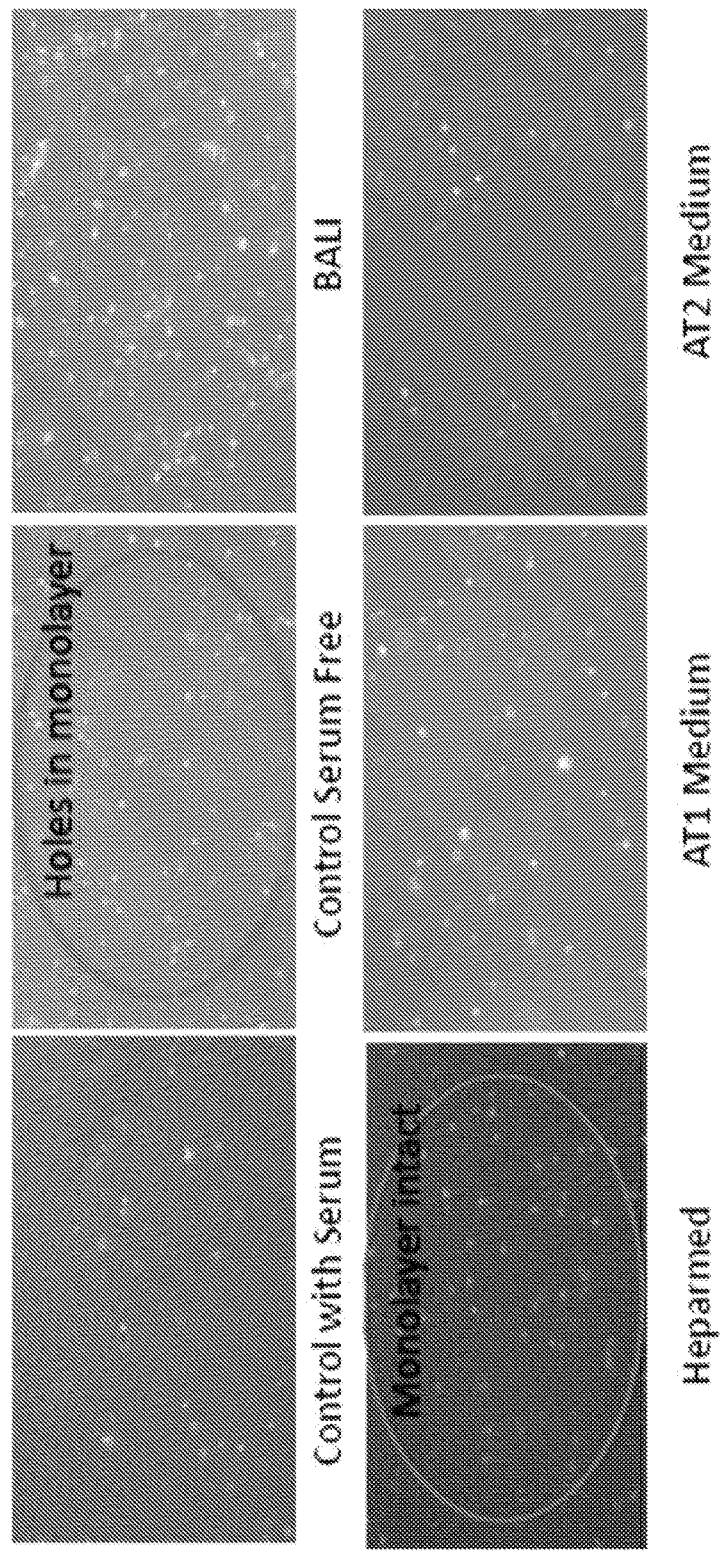
FIG. 2 is a series of digital images of human primary lung microvascular endothelial cells (HLMVECs) cultured for 8 days in the indicated media.

Cor4U cardiomyocytes were cultured in control Cor4U media, 50% Heparmed, or 100% Heparmed (serum-free). The Cor4U cells beat in all three media for up to one month (FIGS. 1A-IC). Contrary to previous belief, serum was not required to sustain Cor4U cells. HLMVECs were also grown in various commercially available media, including serum-free media. Of the commercial media, Heparmed (serum-free) performed best by visual examination (FIG. 2).

Example 3

Custom Media Design

Media formulations used for culturing heart, lung, liver, and kidney were analyzed in silico to determine common components. This included analysis of osmolarity, pH, and buffer capacity, utilizing custom software. Five basal media formulations (Table 1) were designed to meet minimal nutritional requirements of these tissue types. Each of the five media formulations is a complex mixture of 40-106 different components, including differing amounts (molarities) of the components. There are 40 components common to all of the four organs, though many have organ-specific concentrations. A heart formulation includes the basal components plus 18 additional components, a lung formulation includes the basal components plus 33 additional components, and a liver formulations include 34 additional components.

While some of the additional components are common to more than one organ type, 25 components are unique to the liver formulation, 8 are unique to the lung formulations, 3 are unique to the kidney formulation, and 2 are unique to the heart formulation. Most of these organ-specific components are trace elements.

Figure 3A:
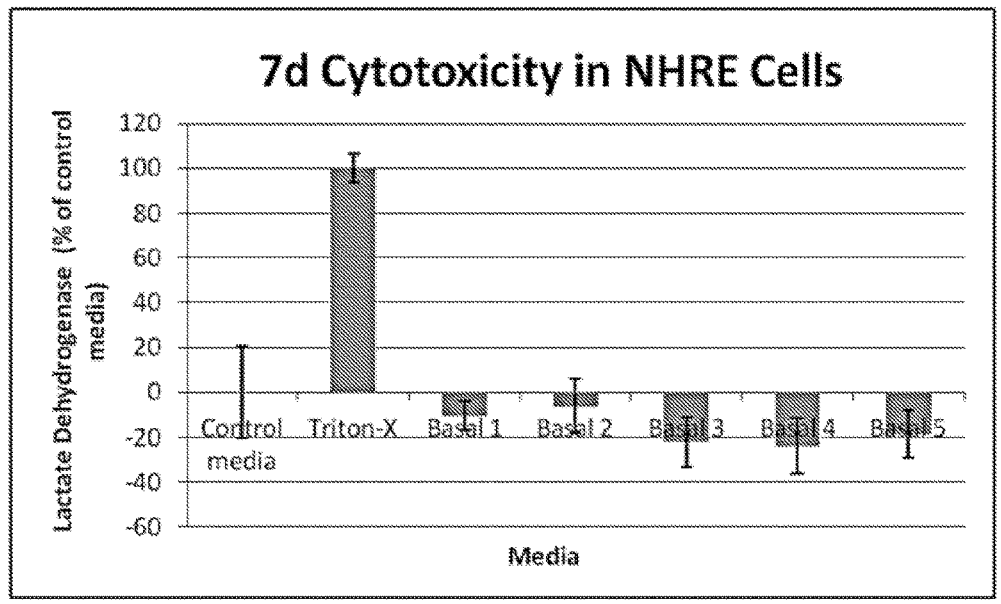
Figure 3B:
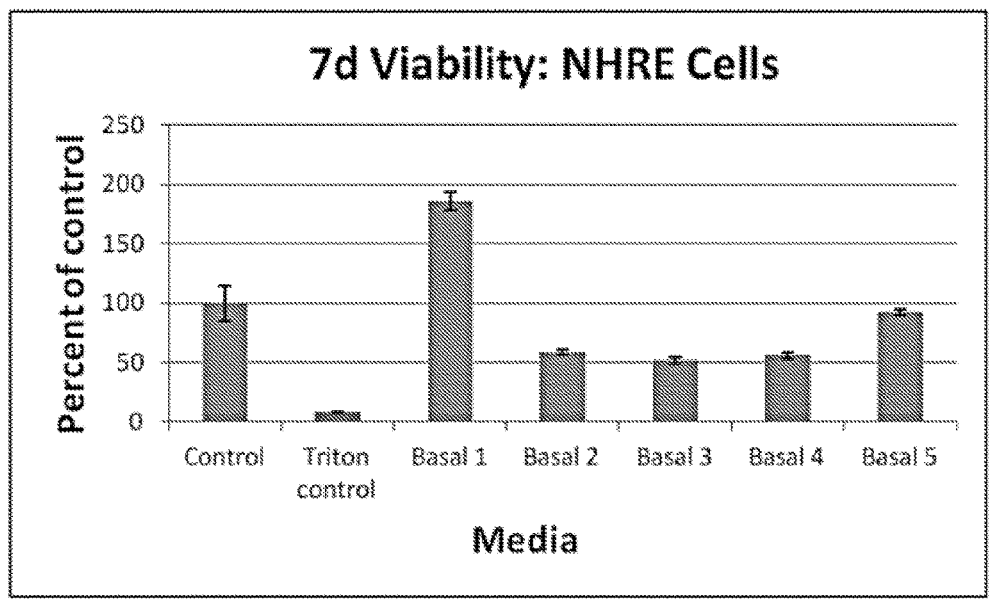
Figure 4A:
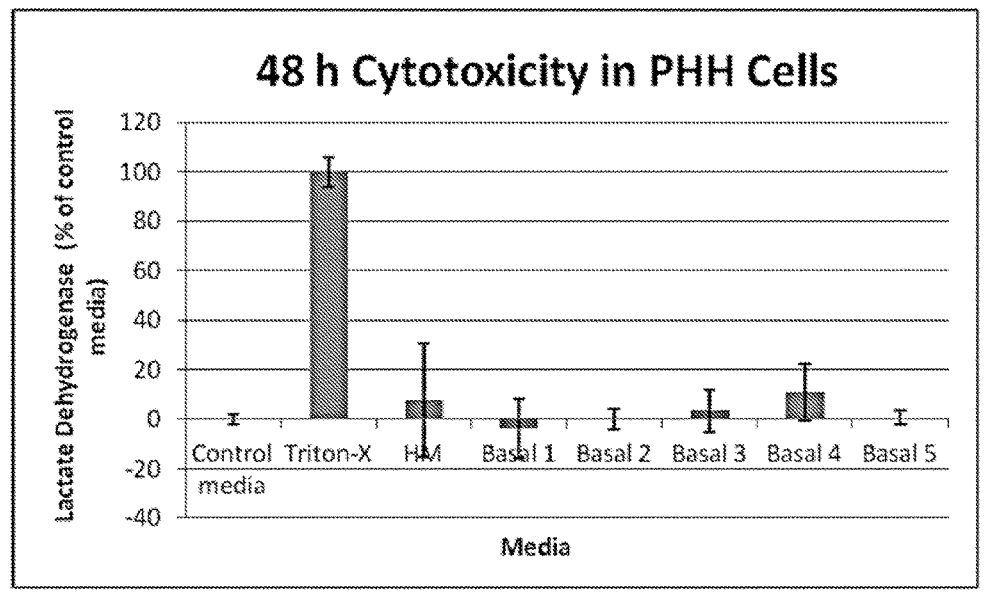
FIGS. 4A and 4B are graphs showing cytotoxicity (FIG. 4A) and cell viability (FIG. 4B) of human frozen primary liver cells (cryopreserved primary human hepatocytes, PHH) cells after 48 hours of culture in the indicated media. The 48 hour time point was utilized due to the expected short life span of this cell type. Control media is Hepatocyte Maintenance Medium (TRL, Research Triangle Park, N.C.). "Triton-X" or "Triton control" indicates cells treated with Triton® X-100 surfactant to disrupt cell membranes and provide a positive control for cell leakage and/or death.
Figure 4B:
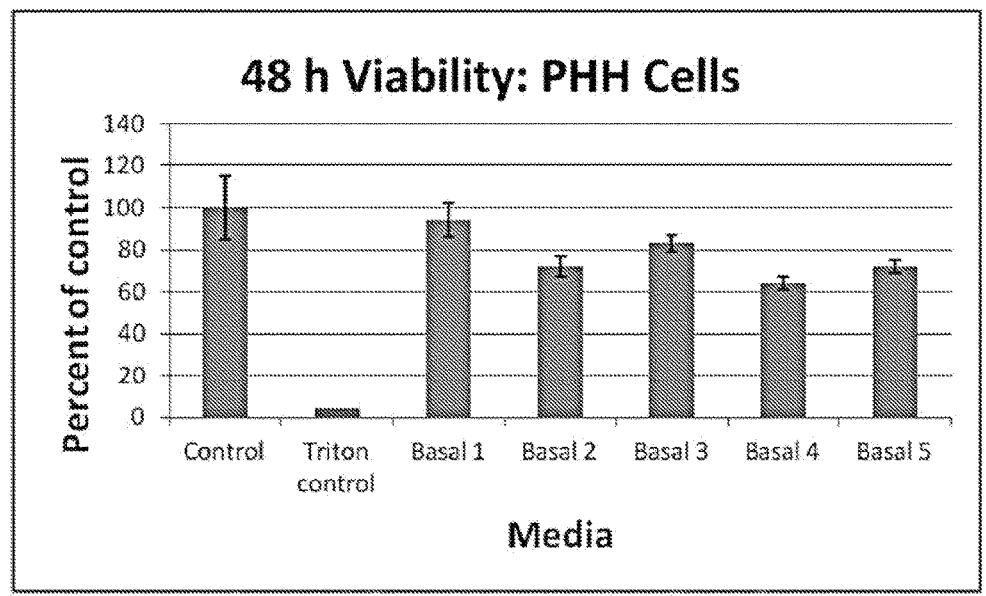
Figure 5A:
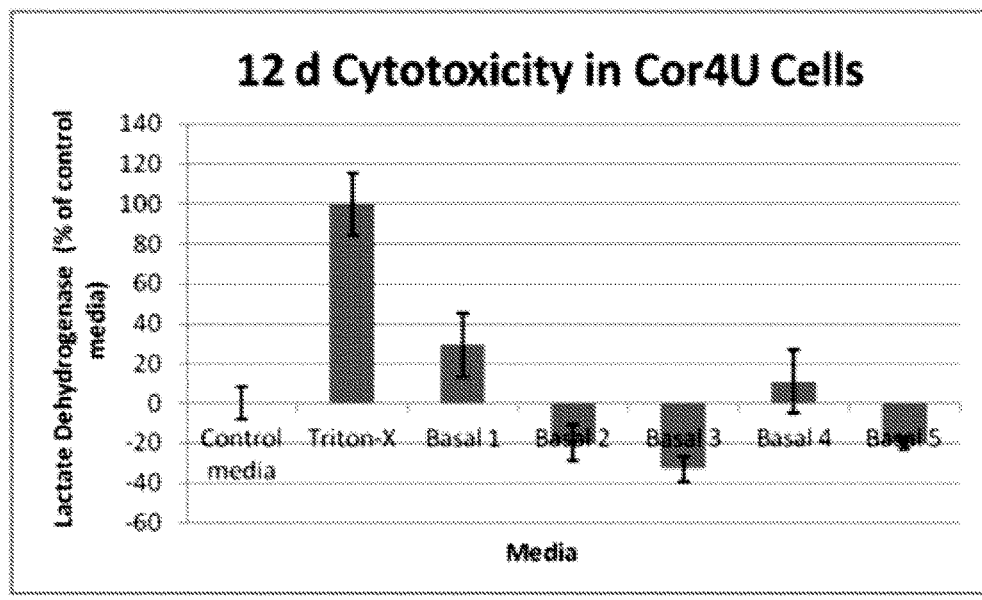
FIGS. 5A and 5B are graphs showing cytotoxicity (FIG. 5A) and cell viability (FIG. 5B) of Cor4U cardiomyocyte cells after 12 days of culture in the indicated media. Control media is Cor4U Culture Medium (Axiogenesis, Plymouth Meeting, Pa.). "Triton-X" or "Triton control" indicates cells treated with Triton® X-100 surfactant to disrupt cell membranes and provide a positive control for cell leakage and/or death.
Figure 5B:
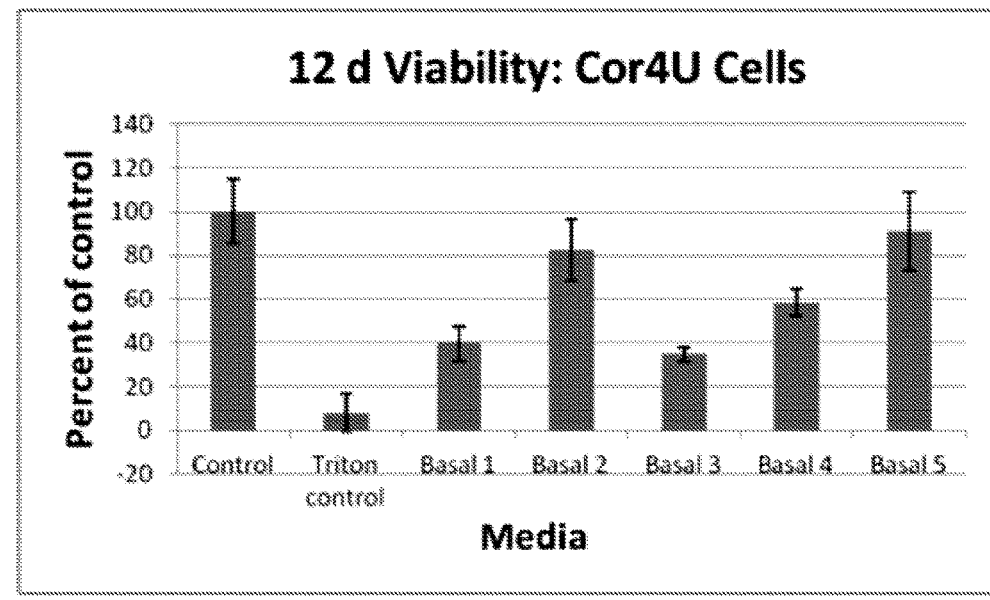
Figure 6A:
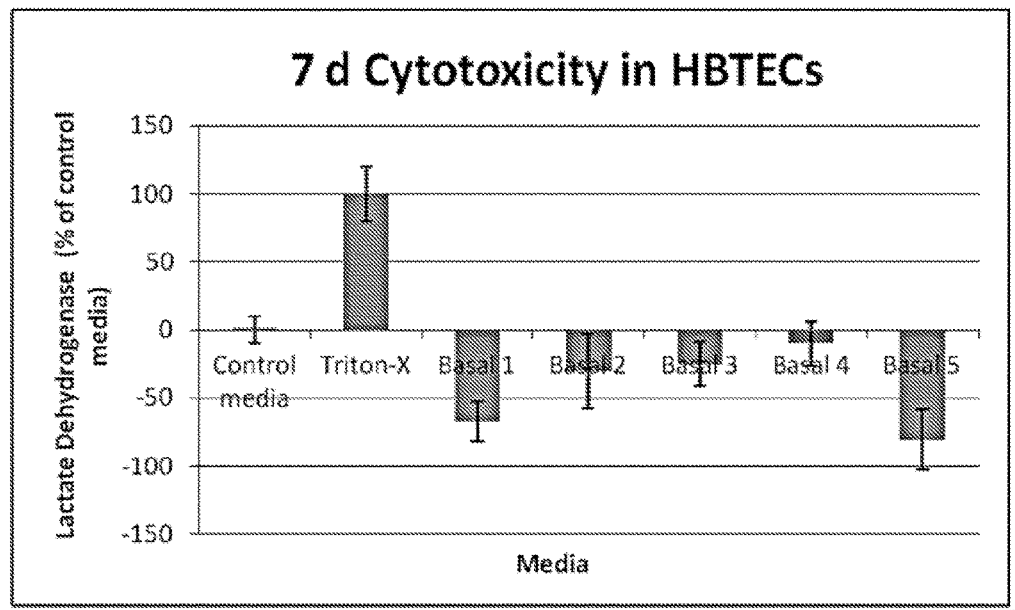
FIGS. 6A and 6B are graphs showing cytotoxicity (FIG. 6A) and cell viability (FIG. 6B) of human primary bronchial/tracheal epithelial cells (HBTEC) after 7 days of culture in the indicated media. Control media is BronchiaLife™ medium (Lifeline Cell Technology). "Triton-X" or "Triton control" indicates cells treated with Triton® X-100 surfactant to disrupt cell membranes and provide a positive control for cell leakage and/or death.
Figure 6B:
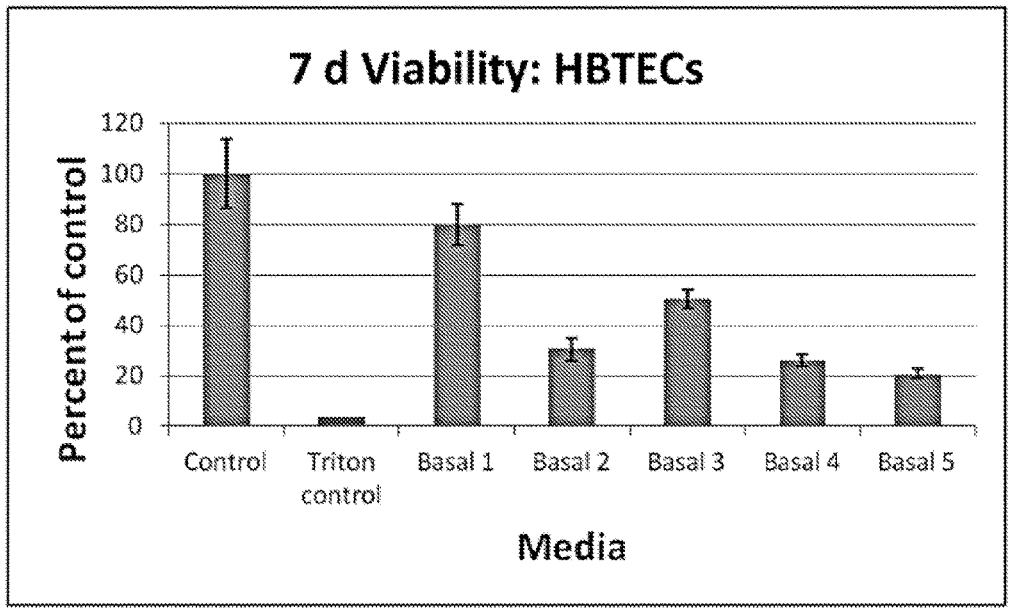

The five basal media formulations include:

Medium 1—a minimum formulation that uses the least amount of components in any organ, or none, if that component is excluded from any organ's formula Medium 2—a minimal formulation that includes a minimum concentration of all of the components Medium 3—a comprehensive formulation that includes an average of compounds required for each organ Medium 4—a heart and liver minimal formulation Medium 5—a heart and liver comprehensive formulation Cytotoxicity (measured by LDH as a percentage of control media) and viability (measured as percent of control) of cells in the five basal media formulations were tested. Primary human renal cells (NHRE, FIGS. 3A and 3B), primary human hepatocytes (PHH, FIGS. 4A and 4B), cardiac iPS cells (Cor4U; FIGS. 5A and 5B), and human bronchial epithelial cells (HBTEC, FIGS. 6A and 6B) were tested. Primary mixed renal epithelial cells maintained their morphology and membrane integrity best in Medium 5 (FIG. 3C). In addition, beating capability of the Cor4U cells was observed in the media formulations (Table 3).

TABLE 3

Beat capability of Cor4U cells in basal media formulations
Beating

| | 24 h | 48 h | 4 d | 6 d | 9 d | 12 d |
|---|---|---|---|---|---|---|
| Control | + | + | + | + | + | + |
| Medium 1 | − | − | + | + | − | − |
| Medium 2 | − | + | + | + | + | + |
| Medium 3 | + | − | − | − | − | − |
| Medium 4 | − | − | − | − | − | − |
| Medium 5 | − | + | + | + | + | + |

Example 4

Additional Testing of Custom Media in Liver Models

This example describes further testing of Media 1-5 in two-dimensional and three-dimensional liver models.

Figure 7A:
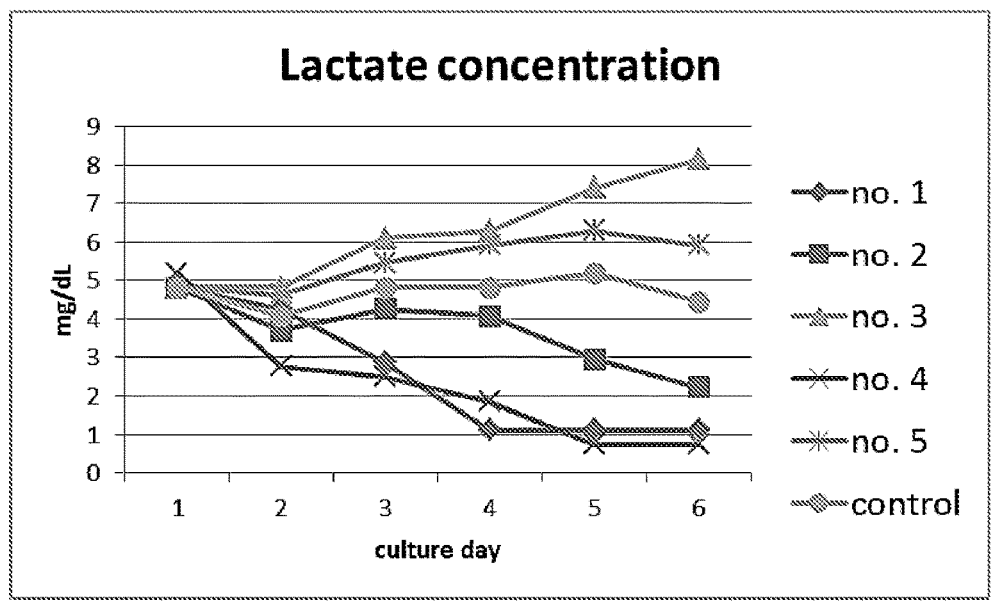
FIGS. 7A-7C are a series of panels showing the effect of various media formulation on primary human hepatocytes.
Figure 7B:
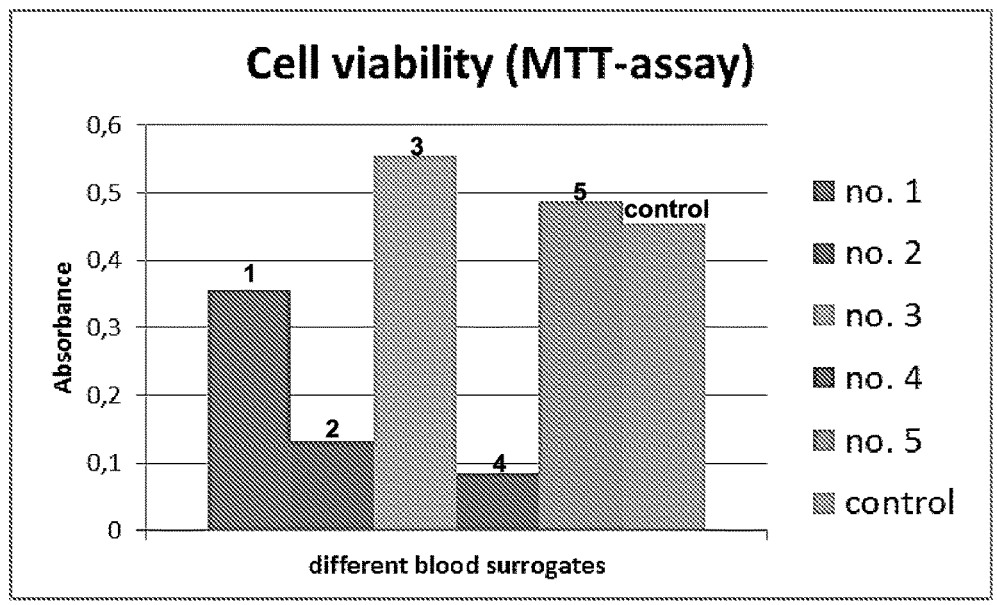
Figure 7C:
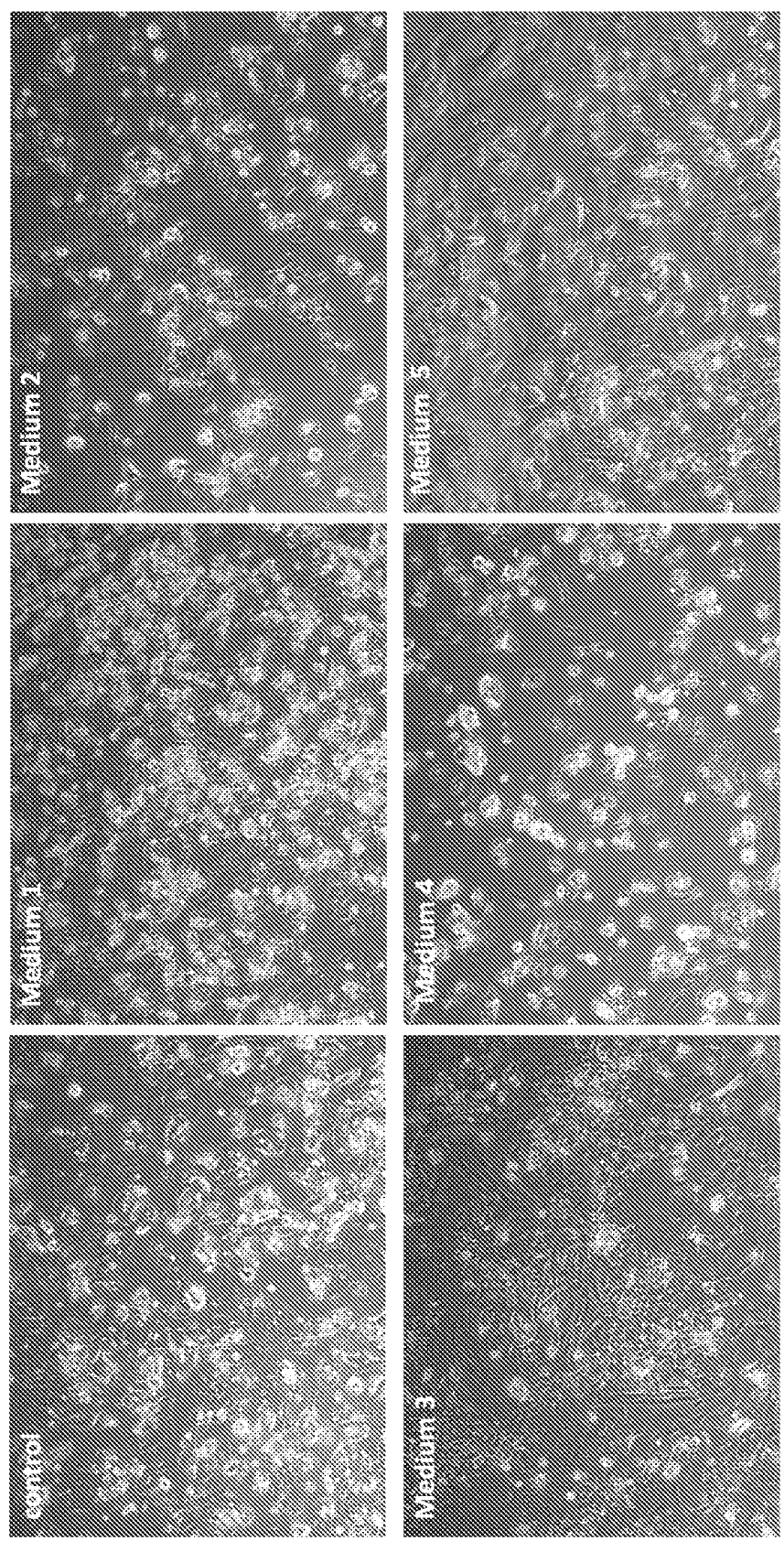

Media 1-5 were tested in a two-dimensional liver construct over six days. Previously frozen primary human hepatocytes were cultures in a monolayer in a control medium (Heparmed, Biochrom, Berlin, Germany), Medium 3, or Medium 5. Lactate concentration was measured daily in the media over the six days of culture (FIG. 7A) and cell viability was measured by the MTT method after six days (FIG. 7B). Cell morphology was also assessed after six days (FIG. 7C). Medium 3 and Medium 5 showed the best performance in this model.

Figure 8A:
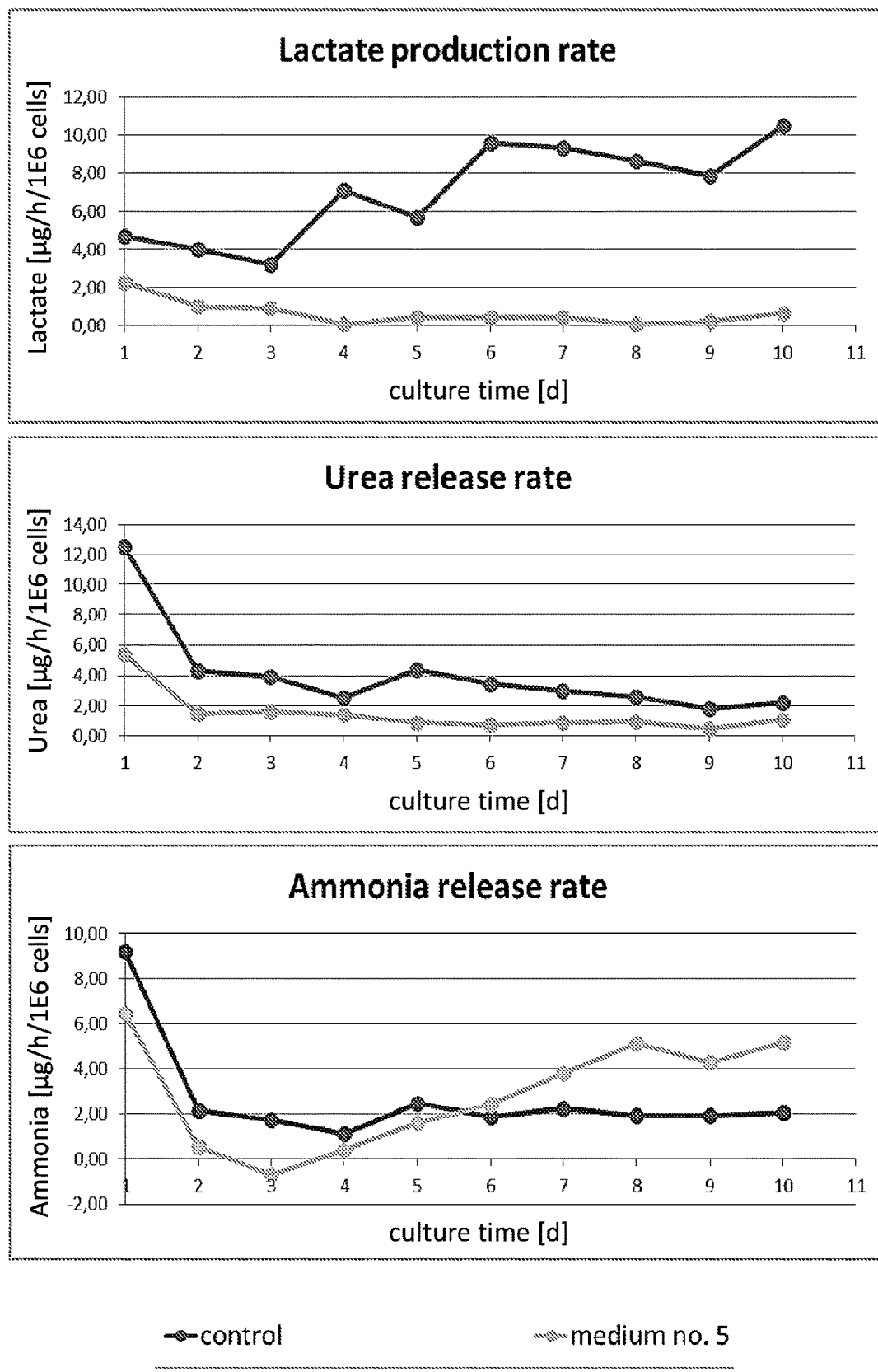
FIGS. 8A-8B are a series of graphs showing function in a three-dimensional liver bioreactor over 10 days of culture with the indicated media.
Figure 8B:
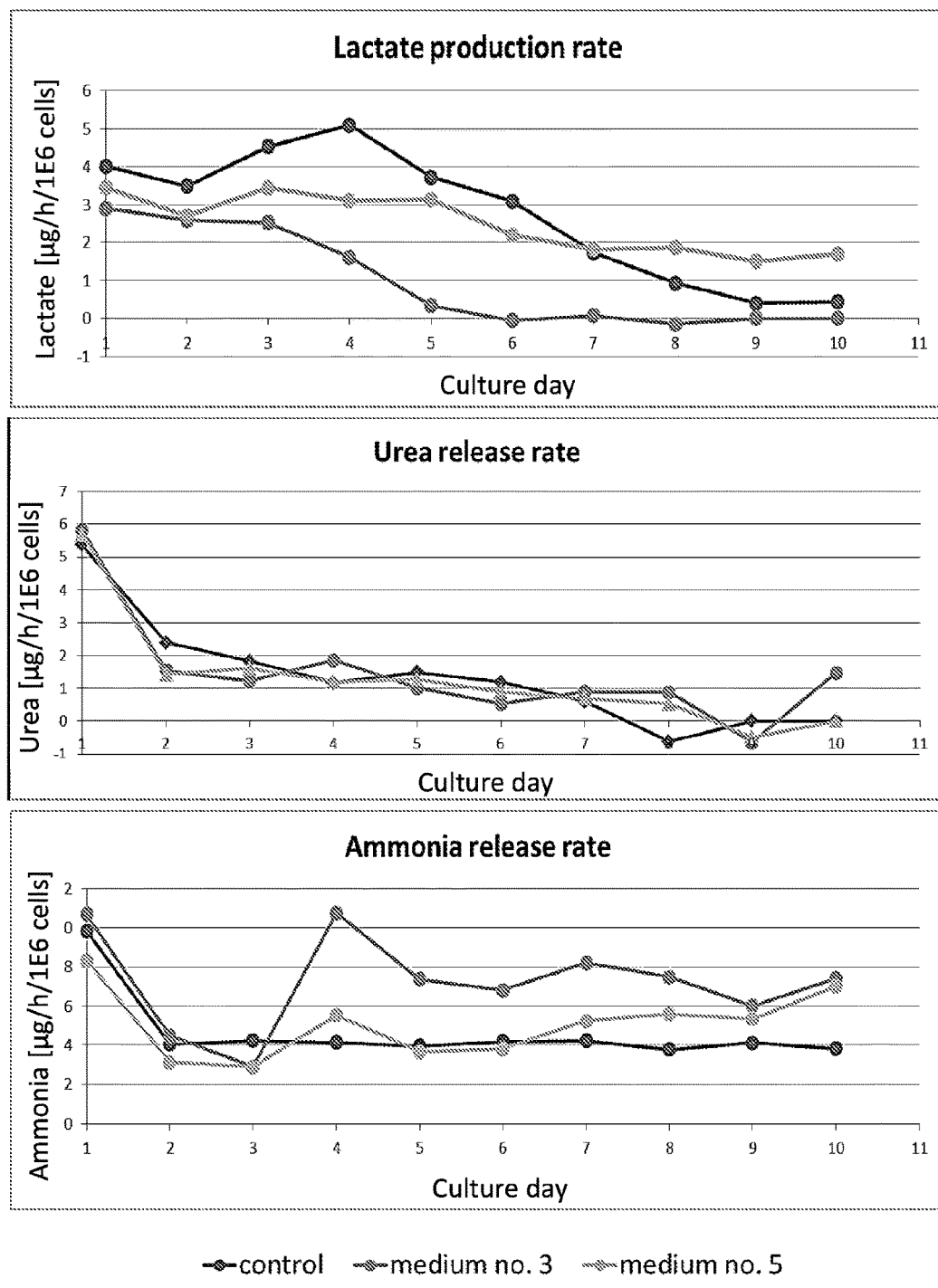

Media 3 and 5 were also tested in a three-dimensional liver bioreactor model. In one set of experiments, Medium 5 was used throughout (FIG. 8A). In another set of experiments, the starting medium was Heparmed and Medium 3 or Medium 5 was added in to the bioreactor at a rate of 3 μl/minute starting on day 3 (FIG. 8B). Medium 5 showed the best performance in this model system.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A system comprising:
(a) a cell or tissue culture medium comprising an aqueous solution comprising 92.0 mM NaCl, 3.43 mM KCl, 1.00 mM $CaCl_2 \cdot 2H_2O$, 0.453 mM $NaH_2PO_4$, 0.407 mM $MgSO_4$, 0.696 nM $ZnSO_4 \cdot 7H_2O$, 0.248 nM $Fe(NO_3)_3 \cdot 9H_2O$, 0.699 mM L-arginine, 0.450 mM L-leucine, 0.415 mM L-isoleucine, 0.250 mM glycine, 0.215 mM L-phenylalanine, 0.0499 mM L-alanine, 0.0500 mM L-asparagine, 0.250 mM L-serine, 0.221 mM L-valine, 0.150 mM L-histidine, 0.150 mM L-proline, 0.0442 mM L-tryptophan, 0.116 mM L-methionine, 0.301 mM L-lysine, 0.0500 mM L-glutamic acid, 0.998 mM L-cysteine, 0.227 mM sodium pyruvate, 0.0165 mM niacinamide/nicotinamide, 0.0111 mM myoinositol/inositol, 0.0107 mM choline chloride, 9.71 μM pyridoxine, 6.43 μM thiamine, 2.27 μM folic acid, 2.10 μM D-calcium pantothenate, 0.148 μM vitamin B-12, 0.133 μM riboflavin, 0.0143 μM D-biotin, 14.3 mM sodium bicarbonate, 0.499 μM DL-6,8-thioctic acid/lipoic acid, 0.125 mg/L transferrin, 0.360 mg/L $CuSO_4 \cdot 5H_2O$, and 0.0380 nM $Na_2SeO_3$; and
(b) (i) primary cells or tissue wherein the primary cells or tissue comprises one or more kidney, liver, or lung cells or tissue; or
(ii) one or more organ devices, which comprises a kidney, liver, or lung organ device or a combination thereof,
wherein the cell or tissue culture medium contacts the primary cells, tissue, or organ device in vitro.

2. The system of claim 1, wherein the cell or tissue culture medium further comprises an aqueous solution comprising 0.500 mM $Na_2HPO_4$, 1.50 μM $FeSO_4 \cdot 7H_2O$, 0.301 nM $MgCl_2$, 0.0150 mM L-aspartic acid, 0.0168 mM L-tyrosine disodium, 0.684 mM L-alanyl-L-glu, 2.00 mM L-glutamine, 0.449 mM L-threonine, 0.199 mM L-tyrosine disodium salt dihydrate, 0.100 mM L-cystine, 2.78 mM D-fructose, 5.55 mM D-galactose, 5.49 mM D-sorbitol, 1.00 mM sodium acetate anhydrous, 0.0900 mM adenine, 0.252 μM vitamin $D_2$, 0.0164 mM $Na_2EDTA \cdot H_2O$, 0.546 μM D-pantothenic acid hemicalcium, 0.497 μM putrescine, 0.546 μM pyridoxal, 0.0212 μM L-tocopherol acetate, 1.51 μM thymidine, 0.304 μM vitamin A acetate, 0.989 mM sodium propionate, 0.150 μM linoleic acid, 0.0170 μM methyl linoleate, 0.0164 mM arachidonic acid, 8.97 μM penicillin, 2.20 μM xanthine, 0.861 nM insulin, 0.0376 μM bovine serum albumin, 0.0100 μM VEGF, 1.00 nM bFGF, 0.100 μM triiodothyronine, 11.3 mM HEPES free acid, 0.0150 mM polyoxyethylene 20 sorbitan monooleate, 0.0133 mM hypoxanthine, 2.70 μM uracil, 0.0999 μM retinoic acid, 0.500 nM EGF, 0.0370 μM hydrocortisone, 8.19 nM ethanolamine, 0.861 nM glucagon, 0.0100 g/L bovine pituitary extract, 1.00 μM epinephrine, 0.500 μM phosphorylethanolamine, 0.0500 mM silicon, 1.71 nM vanadium, 1.14 nM manganese, 0.100 μM molybdenum, 0.100 μM $NiSO_4$, 3.10 nM tin, 2.87 nM $GeO_2$, 2.47 nM $CrK(SO_4)_2$, 6.00 nm $AlCl_3$, 1.14 nM $MnCl_2$, 0.482 nM KI, 0.421 nM $NiCl_2$, 0.210 nM KBr, 0.207 nM $Na_2MoO_4$, 0.0331 nM RbCl, 0.0209 nM AgCl, and 8.41 pM $CoCl_2$.

3. A method of culturing one or more cell types, one or more tissues, or one or more organs, comprising incubating the system of claim 2 under conditions sufficient to maintain the viability, function, and/or growth of the one or more cells, tissue, or organ devices, wherein the one or more cell or tissue types comprise one or more primary heart cell or tissue types, or wherein the one or more organ devices comprise a kidney, liver, or lung organ device.

4. The cell or tissue culture medium of claim 1, further comprising glucose.

5. A system, comprising:
(a) a cell or tissue culture medium comprising an aqueous solution comprising 106 mM NaCl, 4.76 mM KCl, 1.63 mM $CaCl_2.2H_2O$, $NaH_2PO_4$, 0.609 mM $MgSO_4$, 0.750 µM $ZnSO_4.7H_2O$, 0.0620 µM $Fe(NO_3)_3.9H_2O$, 0.250 mM $Na_2HPO_4$, 0.750 µM $FeSO_4.7H_2O$, 0.151 mM $MgCl_2$, 1.53 mM L-aspartic acid, 1.78 mM L-arginine, 1.48 mM L-leucine, 1.46 mM L-isoleucine, 1.13 mM glycine, 1.11 mM L-phenylalanine, 1.02 mM L-alanine, 0.805 mM L-tyrosine disodium, 0.775 mM L-asparagine, 0.625 mM L-serine, 0.610 mM L-valine, 0.575 mM L-histidine, 0.575 mM L-proline, 0.342 mM L-alanyl-L-glu, 0.272 mM L-tryptophan, 0.209 mM L-methionine, 0.400 mM L-lysine, 0.175 mM L-glutamic acid, 0.118 mM L-cysteine, 1.28 mM L-glutamine, 0.225 mM L-threonine, 0.107 mM L-tyrosine disodium salt dihydrate, 0.0500 mM L-cystine, 1.51 mM sodium pyruvate, 1.39 mM D-fructose, 2.78 mM D-galactose, 2.75 mM D-sorbitol, 0.500 mM sodium acetate anhydrous, 0.0492 mM niacinamide/nicotinamide, 0.0406 mM myoinositol/inositol, 0.0374 mM choline chloride, 9.79 µM pyridoxine, 6.43 µM thiamine, 4.14 µM folic acid, 3.40 µM D-calcium pantothenate, 0.325 µM vitamin B-12, 0.358 µM riboflavin, 1.03 µM D-biotin, 0.126 µM vitamin $D_2$, 8.20 µM $Na_2EDTA.H_2O$, 0.252 µM putrescine, 0.273 µM pyridoxal, 0.0106 µM D,L-tocopherol acetate, 0.754 µM thymidine, 0.152 µM vitamin A acetate, 0.495 mM sodium propionate, 8.97 µM linoleic acid, 8.50 nM methyl linoleate, 8.20 µM arachidonic acid, 0.0850 mM penicillin, 20.2 mM sodium bicarbonate, 0.739 µM DL-6,8-thioctic acid/lipoic acid, 5.30 mg/L transferrin, 7.52 µM xanthine, 0.500 µM insulin, 0.0188 µM bovine serum albumin, 5.00 nM VEGF, 0.500 nM bFGF, 0.0500 nM triiodothyronine, 0.431 nM glucagon, 0.855 nM vanadium, 0.571 nM manganese, 1.55 nM tin, 2.78 nM $CuSO_4.5H_2O$, 1.44 nM $GeO_2$, 1.24 nM $CrK(SO_4)_2$, 3.00 nM $AlCl_3$, 0.570 nM $MnCl_2$, 0.241 nM KI, 0.211 nM $NiCl_2$, 0.105 nM KBr, 0.104 nM $Na_2MoO_4$, 0.0160 µM $Na_2SeO_3$, 0.0166 nM RbCl, 0.0105 nM AgCl, and 4.21 pM $CoCl_2$; and
(b) (i) primary cells or tissue wherein the primary cells or tissue comprises one or more kidney, liver, or lung cells or tissue; or
(ii) one or more organ devices, which comprises a kidney, heart, liver, or lung organ device or a combination thereof,
wherein the cell or tissue culture medium contacts the primary cells, tissue, or organ device in vitro.

6. A method of culturing one or more cell types, one or more tissues, or one or more organs, comprising incubating the system of claim 5 under conditions sufficient to maintain the viability, function, and/or growth of the one or more cells, tissue, or organ devices, wherein the one or more cell or tissue types comprise one or more primary liver cell or tissue types or one or more primary heart cell or tissue types, or wherein the one or more organ devices comprise a liver or lung organ device.

7. A method, comprising perfusing the system of claim 5, wherein the system comprises the organ device, and the organ device is fluidly coupled to a platform device comprising:
an organ perfusion system in fluid communication with a fresh media circuit and a recirculation circuit, wherein the fresh media circuit is fluidly coupled to the organ device and the recirculation circuit is fluidly coupled to the organ device;
one or more pumps capable of pumping fluid to one or more valves;
a perfusion controller in electrical communication with the organ perfusion system; and
an analyzer, a sensor, or a combination thereof in electrical communication with the perfusion controller, wherein the medium is introduced to the organ device through the fresh media circuit.

8. The method of claim 7, wherein the platform device comprises two or more fluidly coupled organ devices.

9. The method of claim 7, further comprising:
introducing a compound, or composition containing a compound, into the medium in the fresh media circuit; and
analyzing a response generated by the organ device after the compound, or composition thereof, has been introduced into the platform device.

10. The method of claim 9, further comprising extracting a sample from the platform device.

11. The method of claim 10, further comprising introducing the sample into a chromatograph, a mass spectrometer, or a combination thereof to detect the presence or amount of a response.

12. A method, comprising coupling the system of claim 5, to a reactor with a fluid management device comprising:
one or more channel substrates comprising one or more channels;
a connection substrate comprising one or more inlets and/or outlets;
a valving system comprising one or more valves positioned off-plane of the connection substrate and fluidly coupled to the one or more channels; and
a reservoir comprising:
one or more chambers for housing a fluid;
one or more integrated flow channels located along one or more walls of the one or more chambers; and
one or more ports for delivering fluid to or from the one or more chambers, wherein the fluid management device is fluidly coupled with the reactor and the medium is housed in the reservoir;
and delivering the medium to the reactor.

13. The method of claim 12, wherein the reactor is one or more organ devices.

14. The method of claim 13, wherein the fluid management device is fluidly coupled to an organ perfusion system with a fresh media circuit and a recirculation circuit, wherein the fresh media circuit is coupled to an inlet of the organ device through the fluid management device and the recirculation circuit is fluidly coupled an outlet of the organ device through the fluid management device; and wherein the reactor further comprises:
one or more pumps capable of pumping fluid to one or more valves;
a perfusion controller coupled to the organ perfusion system; and
an analyzer, a sensor, or a combination thereof coupled to the perfusion controller.

15. The method of claim 13, wherein the one or more organ devices comprise a lung device, a heart device, a liver device, a kidney device, or a combination thereof.

16. The method of claim 12, further comprising: introducing a compound, or composition containing a compound, into the medium; and analyzing a response generated by the organ device after the compound, or composition thereof, has been introduced into the organ device.

17. The method of claim 16, further comprising extracting a sample from the platform device.

18. A system comprising
(a) a cell or tissue culture medium comprising an aqueous solution comprising 110 mM NaCl, 4.29 mM KCl, 1.33 mM CaCl$_2$.2H$_2$O, 0.592 mM NaH$_2$PO$_4$, 0.508 mM MgSO$_4$, 1.50 µM ZnSO$_4$.7H$_2$O, 0.0929 µM Fe(NO$_3$)$_3$.9H2O, 0.500 mM Na$_2$HPO$_4$, 1.12 µM FeSO$_4$.7H$_2$O, 0.301 mM MgCl$_2$, 0.766 mM L-aspartic acid, 1.37 mM L-arginine, 1.08 mM L-leucine, 0.937 mM L-isoleucine, 0.688 mM glycine, 0.665 mM L-phenylalanine, 0.538 mM L-alanine, 0.407 mM L-tyrosine disodium, 0.412 mM L-asparagine, 0.575 mM L-serine, 0.593 mM L-valine, 0.370 mM L-histidine, 0.363 mM L-proline, 0.171 mM L-alanyl-L-glu, 0.160 mM L-tryptophan, 0.166 mM L-methionine, 0.450 mM L-lysine, 0.112 mM L-glutamic acid, 0.114 mM L-cysteine, 1.64 mM L-glutamine, 0.349 mM L-threonine, 0.157 mM L-tyrosine disodium salt dihydrate, 0.0751 mM L-cystine, 0.944 mM sodium pyruvate, 0.695 mM D-fructose, 1.39 mM D-galactose, 1.37 mM D-sorbitol, 0.709 mM sodium acetate anhydrous, 0.0332 mM niacinamide/nicotinamide, 0.0552 mM myoinositol/inositol, 0.0855 mM choline chloride, 9.83 µM pyridoxine, 6.43 µM thiamine, 4.93 µM folic acid, 3.92 µM D-calcium pantothenate, 0.326 µM vitamin B-12, 0.470 µM riboflavin, 0.530 µM D-biotin, 0.0225 mM adenine, 0.0630 µM vitamin D2, 4.10 µM Na2EDTA.H2O, 0.136 µM D-calcium pantothenic acid hemicalcium, 0.376 µM putrescine, 0.137 µM pyridoxal, 5.30 nM D,L-tocopherol acetate, 1.13 µM thymidine, 0.0760 µM vitamin A acetate, 0.247 mM sodium propionate, 4.49 µM linoleic acid, 4.25 nM methyl linoleate, 4.10 µM arachidonic acid, 0.0875 mM penicillin, 19.2 mM sodium bicarbonate, 0.0622 µM DL-6,8-thioctic acid/lipoic acid, 3.93 mg/L transferrin, 4.31 µM xanthine, 0.468 µM insulin, 1.89 µM bovine serum albumin, 2.50 nM VEGF, 0.250 M bFGF, 2.79 µM triiodothyronine, 6.58 mM HEPES free acid, 3.75 µM polyoxethylene 20 sorbitan monooleate, 3.32 µM hypoxanthine, 0.675 µM uracil, 0.0500 µM retinoic acid, 0.0151 µM EGF, 0.0343 µM hydrocortisone, 0.127 µM ethanolamine, 0.215 nM glucagon, 2.50 mg/L bovine pituitary extract, 0.250 µM epinephrine, 0.125 µM phosphorylethanolamine, 0.0125 mM silicon, 0.125 µM vanadium, 0.0253 µM manganese, 0.0250 µM molybdenum, 0.0250 µM NiSO$_4$, 0.0133 µM tin, 3.69 nM CuSO$_4$.5H$_2$O, 0.718 nM GeO$_2$, 0.618 nM CrK(SO$_4$)$_2$, 1.50 nM AlCl$_3$, 0.285 nM MnCl$_2$, 0.121 nM KI, 0.105 nM NiCl$_2$, 0.0525 nM KBr, 0.0518 nM Na$_2$MoO$_4$, 0.0124 µM Na$_2$SeO$_3$, 8.28 pM RbCl, 5.23 pM AgCl, and 2.10 pM CoCl$_2$; and
(b) (i) primary cells or tissue wherein the primary cells or tissue comprises one or more kidney, heart, liver, or lung cells or tissue; or
(ii) one or more organ devices, which comprises a kidney, heart, liver, or lung organ device or a combination thereof,
wherein the cell or tissue culture medium contacts the primary cells, tissue, or organ device in vitro.

19. A method of culturing one or more cell types, one or more tissues, or one or more organs, comprising incubating the system of claim 5 under conditions sufficient to maintain the viability, function, and/or growth of the one or more cells, tissue, or organ devices, wherein the one or more cell or tissue types comprise one or more primary kidney cell or tissue types, or one or more primary liver cell or tissue types, or one or more primary lung cell or tissue types, or wherein the one or more organ devices comprise a liver, or lung organ device.

20. A method of culturing one or more cell types, one or more tissues, or one or more organs, comprising incubating the system of claim 18 under conditions sufficient to maintain the viability, function, and/or growth of the one or more cells, tissue, or organ devices, wherein the one or more cell or tissue types comprise one or more primary liver cell or tissue types or one or more primary lung cell or tissue types, or wherein the one or more organ devices comprise a liver or lung organ device.

* * * * *